United States Patent [19]
Taylor et al.

[11] Patent Number: 5,654,421
[45] Date of Patent: Aug. 5, 1997

[54] AUTOMATIC DISHWASHING COMPOSITIONS COMPRISING QUATERNARY SUBSTITUTED BLEACH ACTIVATORS

[75] Inventors: Lucille Florence Taylor, Middletown; Mark Robert Sivik, Fairfield; Alan David Willey, Cincinnati; James Charles Theophile Burckett-St. Laurent, Cincinnatti; Frederick Anthony Hartman, Cincinnatti, all of Ohio

[73] Assignee: The Procter & Gamble Company, Cincinnati, Ohio

[21] Appl. No.: 486,654

[22] Filed: Jun. 7, 1995

Related U.S. Application Data

[62] Division of Ser. No. 298,904, Aug. 31, 1994, Pat. No. 5,578,136.

[51] Int. Cl.$^6$ .................. C07D 223/10; C07D 207/263; C11D 3/28; C11D 3/395
[52] U.S. Cl. ................ 540/531; 540/458; 546/243; 510/220
[58] Field of Search ................ 540/531, 485; 546/243

[56] References Cited

U.S. PATENT DOCUMENTS

| | | | |
|---|---|---|---|
| 3,988,433 | 10/1976 | Benedict | 424/53 |
| 4,260,529 | 4/1981 | Letton | 252/547 |
| 4,397,757 | 8/1983 | Bright et al. | 252/186.41 |
| 4,539,130 | 9/1985 | Thompson et al. | 252/94 |
| 4,751,015 | 6/1988 | Humphreys et al. | 252/99 |
| 4,818,426 | 4/1989 | Humphreys et al. | 252/99 |
| 4,904,406 | 2/1990 | Darwent et al. | 252/102 |
| 4,933,103 | 6/1990 | Aoyagi et al. | 252/186.38 |
| 4,988,451 | 1/1991 | Nunn et al. | 252/95 |
| 5,059,344 | 10/1991 | Aoyagi et al. | 252/186.38 |
| 5,093,022 | 3/1992 | Sotoya et al. | 252/102 |
| 5,106,528 | 4/1992 | Francis et al. | 252/186.23 |
| 5,143,641 | 9/1992 | Nunn | 252/186.38 |
| 5,245,075 | 9/1993 | Venturello et al. | 560/302 |
| 5,269,962 | 12/1993 | Brodbeck et al. | 252/186.25 |
| 5,294,362 | 3/1994 | Venturello et al. | 252/102 |

FOREIGN PATENT DOCUMENTS

| | | | |
|---|---|---|---|
| 284 292 | 3/1988 | European Pat. Off. | 3/39 |
| 458 396 A1 | 5/1991 | European Pat. Off. | 3/39 |
| 475 512 A1 | 9/1991 | European Pat. Off. | 219/4 |
| 2-115154 | 10/1988 | Japan | C07C 237/52 |
| 1382594 | 2/1975 | United Kingdom . | |
| WO94/01399 | 1/1994 | WIPO | 409/40 |
| WO94/02597 | 2/1994 | WIPO | C12N 9/28 |
| WO94/07944 | 4/1994 | WIPO | C08K 3/00 |

*Primary Examiner*—Robert T. Bond
*Attorney, Agent, or Firm*—Michael D. Jones; Brian M. Bolam; Kim W. Zerby

[57] ABSTRACT

Automatic dishwashing detergent compositions, comprising particular quaternary-substituted bleach activators, are provided. More specifically, the invention relates to granular automatic dishwashing detergents which provide enhanced cleaning/bleaching benefits through the selection of quaternary-substituted bleach activators having specific features, such as caprolactam or valerolactam leaving groups and/or the ability to form particular cationic aliphatic peracid structures in solution. Preferred automatic dishwashing compositions comprise amylase enzymes. Included are preferred activator compounds and methods for washing tableware in domestic automatic dishwashing appliances using the activators.

4 Claims, No Drawings

AUTOMATIC DISHWASHING COMPOSITIONS COMPRISING QUATERNARY SUBSTITUTED BLEACH ACTIVATORS

This is a division of application Ser. No. 08/298,904, filed on Aug. 31, 1994, now U.S. Pat. No. 5,578,136.

TECHNICAL FIELD

The present invention is in the field of automatic dishwashing detergents comprising bleach. More specifically, the invention encompasses granular automatic dishwashing detergents comprising selected bleach activators which contain quaternary nitrogen. Preferred activators and methods for washing tableware are included.

BACKGROUND OF THE INVENTION

Automatic dishwashing, particularly in domestic appliances, is an art very different from fabric laundering and institutional dishcare. Institutional dishwashing can be done with strong alkali under carefully controlled conditions, whereas domestic dishwashing is done in an environment in which strong alkalis are potentially hazardous. Domestic fabric laundering is normally done in purpose-built machines having a tumbling action. These are very different from spray-action domestic automatic dishwashing appliances. The spray action in the latter tends to cause foam. Foam can easily overflow the low sills of domestic dishwashers and slow down the spray action, which in turn reduces the cleaning action. Thus in the distinct field of domestic machine dishwashing, the use of common foam-producing laundry detergent surfactants is normally restricted. These aspects are but a brief illustration of the unique formulation constraints in the domestic dishwashing field.

Automatic dishwashing with bleaching chemicals is different from fabric bleaching. In automatic dishwashing, use of bleaching chemicals involves promotion of soil removal from dishes, though soil bleaching may also occur. Additionally, soil antiredeposition and anti-spotting effects from bleaching chemicals would be desirable. Some bleaching chemicals, (such as a hydrogen peroxide source together with tetraacetylethylenediamine, TAED) can, in certain circumstances, be helpful for cleaning dishware, but this technology gives far from satisfactory results in a dishwashing context: for example, ability to remove tough tea stains is limited, especially in hard water, and requires rather large amounts of bleach. Other bleach activators developed for laundry use can even give negative effects, such as creating unsightly deposits, when put into an automatic dishwashing product, especially when they have overly low solubility. Other bleach systems can damage items unique to dishwashing, such as silverware, aluminium cookware or certain plastics.

In contrast to typical institutional tableware, consumer glasses, dishware and flatware, especially decorative pieces, as washed in domestic automatic dishwashing appliances, are often susceptible to damage and can be expensive to replace. Typically, consumers dislike having to separate finer pieces and would prefer the convenience and simplicity of being able to combine all their tableware and cooking utensils into a single, automatic washing operation. Yet doing this as a matter of routine has not yet been achieved.

On account of the foregoing technical constraints as well as consumer needs and demands, automatic dishwashing detergent (ADD) compositions are undergoing continual change and improvement. Moreover environmental factors such as the restriction of phosphate, the desirability of providing ever-better cleaning results with less product, providing less thermal energy, and less water to assist the washing process, have all driven the need for improved ADD compositions.

A recognized need in ADD compositions is to have present one or more ingredients which improve the removal of tea stains from consumer articles. Strong alkalis like sodium hydroxide, bleaches such as hypochlorite, builders such as phosphates and the like can help in varying degrees but all can also be damaging to, or leave a film upon, glasses, dishware or silverware. Accordingly, milder ADD compositions have been developed. These make use of a source of hydrogen peroxide, optionally with a bleach activator such as TAED, as noted. Further, enzymes such as commercial amylolytic enzymes (e.g., TEKMAMYL® available from Novo Nordisk S/A) can be added. The alpha-amylase component provides at least some benefit in the starchy soil removal properties of the ADD. ADD's containing amylases typically can deliver a somewhat more moderate wash pH in use and can remove starchy soils while avoiding delivering large weight equivalents of sodium hydroxide on a per-gram-of-product basis. It would therefore be highly desirable to secure improved bleach activators specifically designed to be compatible in ADD formulations, especially with enzymes such as amylases. A need likewise exists to secure better amylase action in the presence of bleach activators.

It is an object of the instant invention to provide automatic dishwashing compositions, especially compact granular, phosphate-free types, incorporating an improved selection of bleaching ingredients. A further object is the provision of novel quaternary substituted bleach activators. In yet another object, the invention provides fully-formulated ADD compositions with or without amylase enzymes, but especially the former, wherein specific quaternary substituted bleach activators are combined with additional selected ingredients including conventional amylases or bleach-stable amylases, so as to deliver superior tea cleaning results, preferably combined with superior starch cleaning, at the same time as excellent care for consumer tableware and flatware.

BACKGROUND ART

Recent improvements in amylases include WO/94/02597, Novo Nordisk A/S, published Feb. 3, 1994, which describes cleaning compositions, including dishwashing compositions, which incorporate mutant amylases. Additional background is in U.S. Pat. No. 4,539,130, Sep. 3, 1985 incorporated by reference.

British Pat. 1,382,594, published Feb. 5, 1975, discloses certain quaternary substituted bleach activators, as does JP 88-115,154.

Co-pending commonly assigned British Patent Appl. Ser. No. 9407944.9, filed Apr. 21, 1994, P&G Case No. CM705F, and U.S. Pat. Appl. Ser. No. 08/249,581, filed May 25, 1994, P&G Case No. 5261 describe cationic activators and cationic activators in ADD compositions, respectively.

Cationic peracids are known in the art. See U.S. Pat. No. 5,245,075, issued Sep. 14, 1993. and WO 94/01399 published Jan. 20, 1994.

SUMMARY OF THE INVENTION

It has now been discovered that a specific group of improved bleach activators provide unexpected, superior automatic dishwashing detergent, ADD, cleaning performance. Such performance is illustrated by, but not limited to, tea stain removal.

Taken broadly, the present invention encompasses automatic dishwashing detergents comprising (a) an effective mount of a quaternary-substituted bleach activator (QSBA) and (b) an effective mount of a source of hydrogen peroxide.

"Quaternary-substituted" bleach activators herein comprise one or more quaternary or cationic nitrogen atoms: the nitrogen is tetravalent:

Quaternary- Unless otherwise noted, the terms "quaternary" or "tetravalent" refer to nitrogen atoms which participate in either four single bonds, two single bonds and a double bond, one single bond and a triple bond, or two double bonds. In general, bonds to tetravalent nitrogen herein can include N-H bonds and other bonds, such as N-O bonds. In highly preferred QSBA's, all bonds in which each tetravalent or quaternary nitrogen atom participates are bonds to carbon atoms:

Preferred automatic dishwashing detergent compositions herein comprise a QSBA having one or, more preferably, both of the following features:

1. the QSBA provides a quaternary-substituted aliphatic peracid on perhydrolysis;
2. the leaving-group L is selected from the group consisting of caprolactam and valerolactam.

So as to ensure that the QSBA provides a quaternary-substituted peracid on perhydrolysis, all QSBA's forming part of the inventive selection comprise an aliphatic carbon atom directly connected to the —C(O)— moiety immediately preceding a leaving-group, L of the bleach activator. When more than one —C(O)L moiety is present in the bleach activator, at least one such —C(O)L moiety is connected to the QSBA through an aliphatic carbon atom.

In general, the leaving-group L of the QSBA is connected to the moiety —C(O)— at least through a trivalent nitrogen atom as in the preferred caprolactam or valerolactam structure.

A third aspect of the inventive selection involves the incorporation of aromatic moieties into preferred QSBA structures. This can enhance properties of the activator, such as physical properties, while maintaining maximum enzyme compatibility. Achieving this while limiting (and preferably completely eliminating) the possibility of aromatic peracid formation is an important feature of preferred embodiments of the instant invention.

There are greater advantages than expected when amylases are included in the instant ADD formulations, for example better removal of complex food soils which have proteinaceous components. The preferred automatic dishwashing detergent compositions (ADD's) herein further comprise an amylase enzyme so that these benefits can be fully exploited.

The instant ADD's have numerous advantages, for example they are economical, compact, less damaging to consumer tableware than might be expected on the basis of their potent bleaching action, they are not reliant on chlorinated compounds, and they avoid the undesirable use of overly high levels of caustic ingredients. In certain preferred embodiments, they are substantially free of boron.

In more detail, the present invention encompasses ADD compositions wherein said quaternary-substituted bleach activator comprises: a tetravalent nitrogen atom; one or two of each of: a carbonyl moiety, —C(O)— and a leaving-group moiety L; one or two of a spacer moiety, Z; and charge-balancing compatible anions; provided that Z is free from tetravalent nitrogen atoms and that the atom in at least one Z connecting Z to —C(O)— is an aliphatic carbon atom; and wherein said tetravalent nitrogen is covalently connected to —C(O)—L through Z.

When more than one tetravalent nitrogen and more than one leaving-group L is present in a QSBA herein, one tetravalent nitrogen may be connected to a —C(O)L moiety through an aromatic moiety in Z, such that the activator forms both an aliphatic and an aromatic peracid on perhydrolysis. "Charge-balancing" herein indicates that the number of anions and their valency are together selected so as to balance the charge of the bleach activator molecule.

In general, the QSBA's herein can comprise additional —C(O)— moieties and additional moieties similar to Z, not connected to leaving-group moieties. However, in the interest of mass efficiency, this is not preferred.

In a preferred ADD composition, said quaternary-substituted bleach activator is selected from the group consisting of monocationic compounds having the formula: (E—Z—C(O)—L) $(Y^{a-})_{1/a}$ wherein E contains said cationic nitrogen atom, Z is substituted or unsubstituted polyalkylene, arylalkylene, arylpolyalkylene, polyalkylene-arylalkylene or polyallcylenearylpolyalkylene provided that from about 2 to about 16 atoms separate the nitrogen in said moiety E and said moiety —C(O)—; a is 1 or higher; and $(Y^{a-})_{1/a}$ are said charge-balancing compatible anions.

In certain highly preferred ADD composition embodiments, E has the formula $R^1R^2R^3N^+$ wherein any R is independently selected from methyl, ethyl, propyl, butyl, phenyl, benzyl, 1-naphthylmethylene and 2-naphthylmethylene; and wherein Z has formula selected from: —(CH$_2$)$_n$— wherein n is from about 3 to about 12, preferably from about 3 to about 6, and —(C$_6$H$_4$)(CH$_2$)$_{n'}$— wherein n' is from 1 to about 8. To further illustrate, preferred E structures are (CH$_3$)$_3$N$^+$, (CH$_3$)$_2$(C$_6$H$_5$CH$_2$)N$^+$, (CH$_3$)$_2$(Np)N$^+$ and mixtures thereof, wherein Np is said naphthylmethylene.

In the ADD composition embodiments, additional bleach-improving materials can be present. Preferably, these are selected from the group consisting of i) transition-metal bleach catalysts; ii) diacyl peroxides; and iii) mixtures thereof.

Whereas conventional amylases such as TEKMAMYL® may be used with excellent results, preferred ADD compositions can use oxidative stability-enhanced amylases. Such an amylase is available from NOVO. In it, oxidative stability is enhanced from substitution using threonine of the methionine residue located in position 197 of B. Licheniformis or the homologous position variation of a similar parent amylase. See the herein-incorporated U.S. Pat. Appl. Ser. No. 08/249,581, filed May 25, 1994, P&G Case No. 5261 for further description of preferred bleach-stable amylases.

The present invention encompasses granular-form, fully-formulated ADD's, preferably phosphate builder-free and chlorine bleach-free, in which additional ingredients, including other enzymes (especially proteases) are formulated.

From the summary of the ADD compositions hereinabove, it will be apparent that the present invention further encompasses novel QSBA's such as those with the noted features. Examples are $(CH_3)_3N^{+(CH_2)}SC(O)L$ (pTs)- where pTs is p-toluenesulfonate; $(CH_3)_2(C_6H_5CH_2)N^+(CH_2)_5C(O)L$ Cl—; and $LC(O)(p-(C_6H_4)CH_2)N^+(CH_3)_2(CH_2)_5C(O)L$ Cl⁻ wherein L is caprolactam. The present invention, moreover, has quaternary substituted peracid (QSP) embodiments. In contrast to certain teachings of the art, it has unexpectedly been discovered that certain substitution patterns in the tetravalent nitrogen atom and certain selections of counter-ion are particularly desirable for granular automatic dishwashing detergent purposes.

The instant invention also encompasses methods; more particularly, a method of washing tableware in a domestic automatic dishwashing appliance, comprising treating the soiled tableware in an automatic dishwasher with an aqueous alkaline bath comprising an aliphatic cationic peracid, preferably with amylase, more preferably still wherein said method comprises a step of forming said aliphatic cationic peracid in-situ by reacting in said bath a quaternary substituted bleach activator as described hereinabove, and a source of hydrogen peroxide.

As already noted, the invention has advantages, including the excellent combination of tea stain removal, good dishcare, and good overall cleaning aided by a greater flexibility to formulate enzymes, especially amylases.

All parts, percentages and ratios used herein are expressed as percent weight unless otherwise specified. All documents cited are, in relevant part, incorporated herein by reference.

DETAILED DESCRIPTION OF THE INVENTION

Preferred ADD compositions of this invention are substantially free of chlorine bleach. By "substantially free" of chlorine bleach is meant that the formulator does not deliberately add a chlorine-containing bleach additive, such as a chloroisocyanurate, to the preferred ADD composition. However, it is recognized that because of factors outside the control of the formulator, such as chlorination of the water supply, some non-zero amount of chlorine bleach may be present in the wash liquor. The term "substantially free" can be similarly constructed with reference to preferred limitation of other ingredients, such as phosphate builder.

By "effective mount" herein is meant an amount which is sufficient, under whatever comparative test conditions are employed, to enhance cleaning of a soiled surface. Likewise, the term "catalytically effective amount" refers to an amount which is sufficient under whatever comparative test conditions are employed, to enhance cleaning of the soiled surface. In automatic dishwashing, the soiled surface may be, for example, a porcelain cup with tea stain, dishes soiled with simple starches or more complex food soils, or a plastic spatula stained with tomato soup. The test conditions will vary, depending on the type of washing appliance used and the habits of the user. Some machines have considerably longer wash cycles than others. Some users elect to use warm water without a great deal of heating inside the appliance; others use warm or even cold water fill, followed by a warm-up through a built-in electrical coil. Of course, the performance of bleaches and enzymes will be affected by such considerations, and the levels used in fully-formulated detergent and cleaning compositions can be appropriately adjusted.

Oxygen Bleaching System—ADD compositions according to the invention comprise an oxygen bleach system. At a minimum, the oxygen bleach system comprises (a) QSBA as defined herein and (b) an effective amount of a source of hydrogen peroxide. It may be possible to do without a source of hydrogen peroxide, for example, if a Quaternary Substituted Peroxy Acid (QSP) (otherwise known as a quaternary substituted peracid) is used, but this is not preferred. The oxygen bleach system can be further complemented by one or more additional bleach-improving materials. Preferably, these can be selected from the group consisting of: i) transition-metal bleach catalysts; ii) organic peroxides (preferably diacyl peroxides); and iii) mixtures thereof. Quaternary substituted peracids can be used but it is greatly preferred to use the QSBA's. The bleach system may be further complemented by conventional bleach activators. A recently discovered group of such activators useful in automatic dishwashing comprises benzoyl caprolactam and benzoyl valerolactam. Long-known activators such as tetraacetylethylenediamine (TAED), nonanoyl oxybenzenesulfonate (NOBS) or phenyl benzoate can be added to the instant compositions. Even cationic bleach activators of the art may be used, of course subject to limitations. It should be appreciated that, by its very nature, the present invention teaches towards the selection of very particular QSBA or QSP bleaches. According to the present discovery, it would be counterproductive to add significant proportions of bleaching ingredients to the instant compositions which destroy the benefits. Such undesirable bleaching ingredients are illustrated by chlorine bleaches and other known bleaches that adversely affect enzymes. Ideally, the instant compositions are substantially free from such aggressive materials as these.

Quaternary Substituted Bleach Activators The present ADD compositions comprise a quaternary substituted bleach activator (QSBA) or a quaternary substituted peracid (QSP); more preferably, the former.

Preferred QSBA structures for the instant ADD compositions are best visualized through simple examples. One such QSBA is selected from the group consisting of monocationic compounds having the formula:

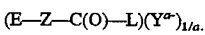

One compound conforming with this formula is:

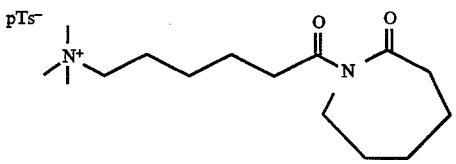

In the above general formula, E is the moiety containing the tetravalent nitrogen atom. Z can be thought of as a "spacer" moiety, exemplified by a penta(methylene) chain. The connection to the carbonyl moiety, —C(O)—, is through an aliphatic carbon atom. L is a leaving-group. Leaving-groups herein comprise a trivalent nitrogen atom through which a covalent connection is made to said —C(O)— moiety. Preferred leaving groups herein are illustrated by caprolactam and valerolactam.

With reference to the above general formula, the $(Y^a)_{1/a}$ are charge-balancing compatible anions. It has been discovered that the proper choice of these anions gives particular advantages to the resulting QSBA's. By the term "compatible anions" is meant that, at a minimum, the anions do not insolubilize the QSBA to such an extent that it cannot operate; nor do they provide any highly bleach-reactive groups. Preferably through the proper selection of monoanions (e.g., p-toluenesulfonate) or polyanions (e.g., polyacrylate), particularly advantageous solubility properties or multi-functionality can be imparted to the QSBA, although in general, dianions, tri-anions etc., can be used provided they are compatible. Also in connection with the anions, it is necessary to define an index, a, depending on the anion valency, so as to balance the total charge. In general, consistent with the full range of anions possible, a is 1 or higher.

Another suitable quaternary substituted bleach activator within the scope of the present invention has the structure:

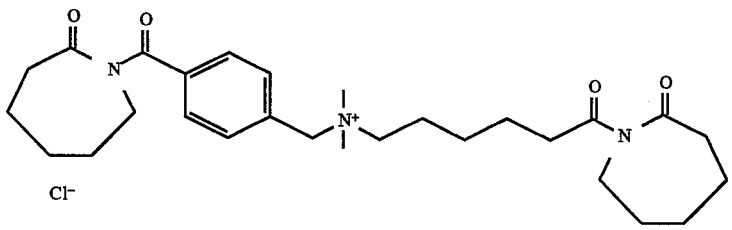

wherein the unfilled valencies are methyl. More generally, this compound can be represented by $(E-(Ar')_m(CH_2)_n-C(O)-L)(Y^{a-})_{1/a}$ wherein: E is $R^1R^2((Ar')_m(CH_2)_n-C(O)-L)N^+$ wherein m and m' are each 0 or 1, provided that m and m' are not both 1, n and n' are each from 0 to about 12, provided that when m is 0, n is not less than 2 and when m' is 0, n' is not less than 2, and all other moieties are as defined elsewhere herein. From this illustration it can be seen that although in general it is preferred herein to provide wholly aliphatic-peracid-forming quaternary bleach activators, it is acceptable, especially in combination with bleach-stable amylase, to formulate the above-illustrated type of quaternary-substituted bleach activator, since it falls within our definition of forming a quaternary-substituted aliphatic peracid on perhydrolysis. Indeed, without being limited by theory, differential reactivity of the two leaving-group sites in the above type of quaternary-substituted bleach activator may offer important advantages to the formulator.

Preferred quaternary substituted bleach activator compounds herein are further illustrated by those of formula $(E-(Ar')_m(CH_2)_n-C(O)-L)(Y^{a'})_{1/a}$ wherein: L is selected from caprolactam and valerolactam; E is $R^1R^2R^3N^+$; Ar' is $(C_6H_4)$; m is 0 or 1; when m is 0, n is from about 3 to about 12 and when m is 1, n is from 1 to about 8; Y is a charge-balancing compatible anion, dianion or polyanion, a is 1 or higher, and $R^1$, $R^2$ and $R^3$ are independently selected from substituted or unsubstituted alkyl, alkaryl, aralkyl, and aryl. A highly preferred QSBA has m=0, n is from about 3 to about 6, and E is independently selected from the group consisting of: $R_3N^+$, $R_2(C_6H_5CH_2)N^+$, $R(C_6H_5CH_2)_2N^+$, $R_2(Np)N^+$, and mixtures thereof, wherein any R is methyl or ethyl and any Np is 1-naphthylmethylene or 2-naphthylmethylene; and said charge-balancing compatible anions are selected from the group consisting of: chloride, sulfate, alkane sulfate, polyacrylate, alkane sulfonate, aryl sulfonate, alkaryl sulfonate and mixtures thereof. In other highly preferred QSBA embodiments, a=1, all R is methyl, and said charge-balancing compatible anions are selected from the group consisting of: methanesulfonate, ethanesulfonate, benzenesulfonate, p-toluenesulfonate, cumenesulfonate, xylenesulfonate, napthalenesulfonate and mixtures thereof.

With reference to the simple preferred embodiments of QSBA's suitable for use in the ADD compositions of the invention, further illustration will now be given of the moieties L, Z, Y and E.

Preferred L/pKa's—The present invention contemplates the use of a cyclic lactam leaving-group with a ring size of from about 6 to about 12 atoms. Preferred leaving-groups are caprolactam and valerolactam. Caprolactam is particularly preferred. Without being bound by theory,-it is believed that certain advantages of the present invention are connected to the choice of leaving group. $pK_a$'s of leaving groups are defined in the art. See for example U.S. Pat. No. 4,283,301. Many art-disclosed leaving-groups for activators have low $pK_a$'s. In contrast, caprolactam and valerolactam are believed to have pKa's above 13. In general, other leaving groups than caprolactam and valerolactam can be substituted for caprolactam and valerolactam in the instant structures provided that they are connected to the structure through a trivalent nitrogen atom and have $pK_a$'s above 13.

Preferred Z—Preferred Z moieties or "spacers" are substituted or unsubstituted polyalkylene, arylalkylene, arylpolyalkylene, polyalkylenearylalkylene or polyalkylene-arylpolyalkylene provided that from about 2 to about 16, preferably from about 2 to about 8, most preferably from about 3 to about 6 atoms separate the nitrogen in said moiety E and said moiety —C(O)—. An aliphatic carbon atom of Z connects to —C(O)L in the activator unless two quaternary centers are present. Preferred Z are further illustrated by —$(Ar')_m(CH_2)_n$— wherein Ar' is o-, m- or p- $(C_6H_4)$; m is 0 or 1, preferably 0; when m=0, n is from about 3 to about 12; when m is 1, n is from 1 to about 8. In general, ether oxygen atoms may optionally be included in Z, provided that the connection to —C(O)L is not made through oxygen.

Preferred Counter-anions (Y)—Preferred compositions of this invention comprise charge-balancing compatible anions or "counter-ions". In general, these may be monovalent, divalent, trivalent or polyvalent. Available anions such as bromide, or phosphates may be used, though they may be other than preferred for one or another reason, such as bleach reactivity or phosphorus content. Compatible anions include chloride. Preferred compatible anions are selected from the group consisting of sulfate, isethionate, alkanesulfonate, alkyl sulfate, aryl sullenate, alkaryl sulfonate, carboxylates, polycarboxylates, and mixtures thereof. Preferred anions include the sulfonates selected from the group consisting of methanesulfonate, ethanesulfonate, benzenesulfonate, p-toluenesulfonate, cumenesulfonate, xylenesulfonate, naphthalene sullenate and mixtures thereof. Especially preferred of these sulfonates are those which contain aryl. Preferred alkyl sulfates include methyl sulfate and octyl sulfate. Preferred polycarboxylate anions suitable herein are nonlimitingly illustrated by terephthalate, polyacrylate, polymaleate, poly (acrylate-comaleate), or similar polycarboxylates; preferably such polycarboxylates have low molecular weights, e.g., 1,000–4, 500. Suitable monocarboxylates are further illustrated by benzoate, naphthoate, p-toluate, and similar hard-water precipitation-resistant monocarboxylates.

Preferred E

In general, E is a moiety containing a cationic nitrogen atom. Preferred E has the formula $R^1R^2R^3N^+$ wherein $R^1$, $R^2$ and R³ (more generally any R) are independently selected from substituted or unsubstituted alkyl, alkaryl and aryl. Preferably any R in moiety E is independently selected from methyl, ethyl, propyl, butyl, phenyl, benzyl, 1-naphthylmethylene and 2-naphthylmethylene. Note that naphthylmethylene moieties are:

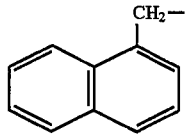

1-Naphthylmethylene

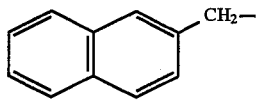

2-Naphthylmethylene

These moieties bond to the remainder of the structure of the QSBA through the indicated unattached valencies. Preferred E are selected from the group consisting of: $R_3N^+$, $R_2(C_6H_5CH_2)N^+$; $R(C_6H_5CH_2)_2N^+$; $R_2(Np)N^+$; and mixtures thereof. In highly preferred QSBA embodiments, E is selected from the group consisting of $(CH_3)_3N^+$, $(CH_3)_2(C_6H_5CH_2)N^+$, $(CH_3)_2(Np)N^+$ and mixtures thereof, most preferably $(CH_3)_2(C_6H_5CH_2)N^+$ and $(CH_3)_2(Np)N^+$. Most generally, noncarbon atoms, such as ether oxygen atoms, can be included in moieties E, such as in the form of an alkylpolyethoxylate chain.

Physical Properties—Preferred QSBA's herein are water-soluble and include compounds which are not significantly surface-active. However, certain preferred QSBA's have a tendency to partition to a definite extent into surfactant micelles, especially into micelles of nonionic surfactants. Therefore, certain preferred quaternary substituted bleach activators of this invention are surface-active, having a critical micelle concentration of less than or equal to about $10^{-2}$ molar, and comprise one long-chain moiety having a chain of from about 8 to about 12 atoms; the counter-ion is preferably non surface-active. Other QSBA's herein are more "hydrophilic" and may have much higher CMC's, e.g., about $10^{-1}$ molar, or higher, especially when the anions are highly water-soluble and non-surface-active.

Other QSBA's—While the foregoing QSBA's include preferred embodiments presented for the purposes of better illustrating the invention, their specific recital should not be taken as limiting. Other QSBA's can readily be contemplated that lie fully within the spirit and scope of the present invention. Examples include modifications of the above structures to make them dicationic, as follows:

Alternately, it is contemplated to "link up" groups E or Z so that they form part of a non-aromatic heterocyclic ring or to make a modification in which the leaving group L has a hydrolytically resistant covalent bond to either group E or group Z; in the latter instance, L is considered a "tethered" leaving group as in either of the structures:

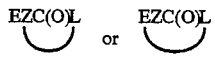

and upon perhydrolysis, still "leaves" the EZC(O) moiety and forms a peracid, such as one having either of the structures:

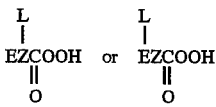

Quaternary Substituted Peracids—Quaternary Substituted Peracids (QSP's) are also suitable for use in the instant ADD compositions. QSP's of this invention generally conform to the QSBA structure with the exception that group L is replaced by a —OOH moiety. QSP's can be made "in situ" or can be preformed by perhydrolyzing the foregoing QSBA's. To be noted, QSP's herein generally contain anions to balance the positive charge derived from the quaternary nitrogen. In the instant ADD compositions, anions are consistent with the definition given for Y hereinabove. Preferred QSP's according to this invention have the formula:$(R^1R^2R^3N^+$—$(Ar')_m(CH_2)_n$—$C(O)$—$OOH)$ $(Y^{a-})_{1/a}$ wherein m is 0 or 1; Ar' is $(C_6H_4)$; when m is 0, n is from about 3 to about 12 and when m is 1, n is from 1 to about 8; a is 1 or higher; Y is selected from the group consisting of p-toluenesulfonate, benzenesulfonate, cumenesulfonate, xylenesulfonate, naphthalene sulfonate, polyacryate, polyacrylate-co-maleate, polymaleate, and mixtures thereof; and $R^1$, $R^2$ and $R^3$ are independently selected from substituted or unsubstituted alkyl, alkaryl and aryl. More highly preferred are QSP's wherein a is 1, m is 0 and at least one of $R^1$, $R^2$ and $R^3$ is selected from benzyl and naphthylmethylene.

Formulation of QSBA or QSP in Product—When required, QSBA's or QSP's can be stabilized in product by a number of means, principal of which are the application of bleach-resistant coatings, such as can be provided by bleach-resistant waxy nonionic surfactants; or by selecting QSBA or QSP structures which contain one or more benzene rings so as to increase the melting-point at least above 30° C. and preferably above 50° C., thereby preventing migration of the QSBA or QSP into the remainder of the composition. Alternatively, or in addition to the foregoing stabilizing approaches, hydrogen peroxide sources, such as sodium

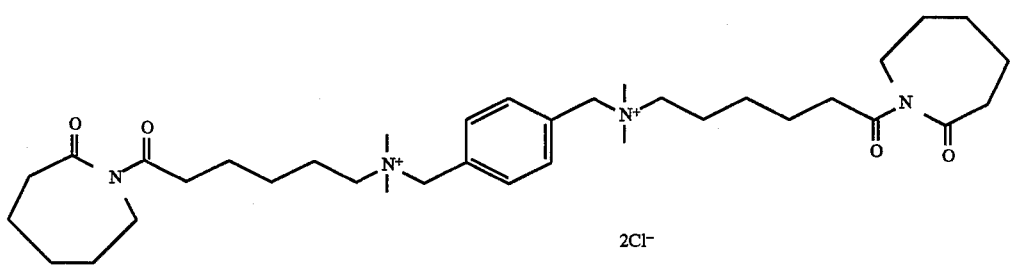

2Cl⁻ percarbonate, can be segregated from the QSBA or QSP by means of organically impermeable silicate or borosilicate coatings.

In general, it should be recognized that QSBA's or QSP's collectively can, in aqueous solution, provide both formally cationic species, such as $(CH_3)_3N^+(CH_2)_5C(O)OOH$ and formally zwittedonic species such as $(CH_3)_3N^+(CH_2)_5C(O)OO^-$. Regardless of whether formally cationic or zwitterionic materials are generated, they remain within the scope of the present invention provided that at least one quaternary nitrogen is present. Again, depending on the precise modification, there may be a plurality of charged sites, requiring in the solid, salt form, a balancing number of onions which can vary widely provided that they do not render the QSBA or QSP substantially insoluble.

Hydrogen Peroxide Source

The ADD compositions herein comprise a QSBA, the level of which can in general vary widely. Preferred levels are generally below 50% and in the preferred embodiments are in the range from about 0.1% to about 10%.

In addition, the instant ADD compositions or bleach systems will generally contain a hydrogen peroxide source, as further defined hereinafter, whenever a QSBA is formulated in the absence of a preformed QSP (such absence is the preferred case). The level of hydrogen peroxide source material can range widely, for example as high as 50% in the composition, more preferably from about 3.3% to about 33%, but lower levels such as from about 1% to about 20% are more typical.

Common hydrogen peroxide source materials include sodium perborates and percarbonates which typically provide up to about 15% of their weight of "available oxygen" for bleaching.

In preferred embodiments of the invention, a hydrogen peroxide source is provided regardless of whether the bleach system otherwise provides bleaching oxygen. The hydrogen peroxide source is typically hydrogen peroxide itself, or a compound which delivers hydrogen peroxide on dissolution, such as is the case with sodium perborate monohydrate, sodium perborate tetrahydrate, sodium percarbonate, or mixtures thereof. Coated forms of these solid hydrogen peroxide sources can be used.

Preferred hydrogen peroxide sources include sodium perborate, commercially available, e.g., in the form of mono- or tetra-hydrate; urea peroxyhydrate, sodium percarbonate, and sodium peroxide. Particularly preferred are sodium perborate, sodium perborate monohydrate and sodium percarbonate. Percarbonate is especially preferred because of environmental issues associated with boron.

Highly preferred percarbonate can be in uncoated or coated form. The average particle size of uncoated percarbonate ranges from about 400 to about 1200 microns, most preferably from about 400 to about 600 microns. If coated percarbonate is used, the preferred coating materials include carbonate, sulphate, silicate, borosilicate, and mixtures thereof. If any coating materials are used here or throughout the specification, such materials are preferably free of fatty carboxylic acid.

The mole ratio of hydrogen peroxide to QSBA in the present ADD compositions preferably ranges from about 20:1 to about 1:1. Highly preferred ratios range from about 15:1 to about 3:1.

Transition Metal Bleach Catalysts—Transition metal bleach catalysts are optional in the present ADD compositions. If used, care will be taken to ensure they do not disrupt the effective working of any enzymes present. Transition-metal bleach catalysts can range from supported or unsupported transition metal salts, including but not limited to those of iron, manganese, copper, cobalt and ruthenium; see for example U.S. Pat. No. 3,398,096 issued Aug. 20, 1968, including simple water-soluble salts of iron and manganese such as the divalent, trivalent, tetravalent and quadrivalent salts; to more recent catalysts such as those of the following references.

One group of catalysts which may be used is one in which the catalyst comprises manganese. Such compounds are well known in the art and include, for example, the manganese-based catalysts disclosed in U.S. Pat. No. 5,246,621, U.S. Pat. No. 5,244,594; U.S. Pat. No. 5,194,416; U.S. Pat. No. 5,114,606; and European Pat. App. Pub. Nos. 549,271A1, 549,272A1, 544,440A2, and 544,490A1; Known examples of these catalysts include:

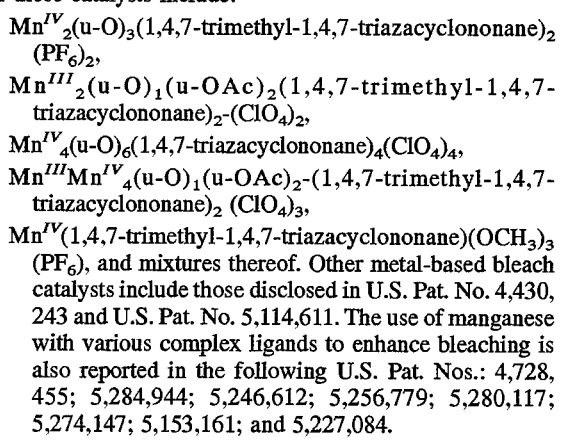

$Mn^{IV}_2(u-O)_3(1,4,7\text{-trimethyl-1,4,7-triazacyclononane})_2(PF_6)_2$, $Mn^{III}_2(u-O)_1(u-OAc)_2(1,4,7\text{-trimethyl-1,4,7-triazacyclononane})_2\text{-}(ClO_4)_2$, $Mn^{IV}_4(u-O)_6(1,4,7\text{-triazacyclononane})_4(ClO_4)_4$, $Mn^{III}Mn^{IV}_4(u-O)_1(u-OAc)_2\text{-}(1,4,7\text{-trimethyl-1,4,7-triazacyclononane})_2(ClO_4)_3$, $Mn^{IV}(1,4,7\text{-trimethyl-1,4,7-triazacyclononane})(OCH_3)_3(PF_6)$, and mixtures thereof. Other metal-based bleach catalysts include those disclosed in U.S. Pat. No. 4,430,243 and U.S. Pat. No. 5,114,611. The use of manganese with various complex ligands to enhance bleaching is also reported in the following U.S. Pat. Nos.: 4,728,455; 5,284,944; 5,246,612; 5,256,779; 5,280,117; 5,274,147; 5,153,161; and 5,227,084.

Iron or Manganese salts of aminocarboxylic acids in general may be useful herein; these include iron and manganese aminocarboxylate salts disclosed for bleaching in the photographic color-processing arts. A particularly useful transition-metal salt herein is derived from ethylenediaminedisuccinate, and any complex of this ligand with iron or manganese can be used. One such catalytic system is described in co-pending commonly assigned U.S. application Ser. No. 08/210,186, filed Mar. 17, 1994.

The bleach catalysts useful in machine dishwashing compositions and concentrated powder detergent compositions may also be selected as appropriate for the present invention. For further examples of bleach catalysts see U.S. Pat. No. 4,246,612 and U.S. Pat. No. 5,227,084.

See also U.S. Pat. No. 5,194,416 which teaches mononuclear manganese (IV) complexes such as $Mn^{IV}(1,4,7\text{-trimethyl-1,4,7-triazacyclononane})\text{—}(OCH_3)_3(PF_6)$.

Further bleach catalysts are disclosed in U.S. Pat. No. 5,114,606 and U.S. Pat. No. 5,114,611. Other examples include Mn gluconate, $Mn(CF_3SO_3)_2$, $Co(NH_3)_5Cl$, and the binuclear Mn complexed with tetra-N-dentate and bi-N-dentate ligands, including $N_4Mn^{III}(u-O)_2Mn^{IV}N_4)^+$and $[Bipy_2Mn^{III}(u-O)_2Mn^{IV}bipy_2]\text{—}(ClO_4)_3$.

The bleach catalysts of the present invention may also be prepared by combining a water-soluble ligand with a water-soluble transition metal salt such as one of manganese in aqueous media, optionally further concentrating the resulting mixture by evaporation. Any convenient water-soluble salt of the transition metal can be used herein provided that the metal is one known to react with hydrogen peroxide. The (II), (III), (IV) and/or (V) oxidation states or higher, depending on choice of metal, may be used. In some instances, sufficient transition metal may inherently be present in the wash liquor, but, in general, it is preferred to dose transition-metal cations in the compositions to ensure metal presence in catalytically-effective amounts.

Other bleach catalysts are described, for example, in European Pat. App. Pub. Nos. 408,131 (cobalt complex catalysts), 384,503, and 306,089 (metallo-porphyrin catalysts), U.S. Pat. No. 4,728,455 (manganese/multidentate ligand catalyst), U.S. Pat. No. 4,711,748 and European Pat. App. Pub. No. 224,952, (absorbed manganese on aluminosilicate catalyst), U.S. Pat. No. 4,601,845 (aluminosilicate support with manganese and zinc or magnesium salt), U.S. Pat. No. 4,626,373 (manganese/ligand catalyst), U.S. Pat. No. 4,119,557 (ferric complex catalyst), German Pat. specification 2,054,019 (cobalt chelant catalyst) Canadian 866,191 (transition metal-containing salts), U.S. Pat. No. 4,430,243 (chelants with manganese cations and non-catalytic metal cations), and U.S. Pat. No. 4,728,455 (manganese gluconate catalysts).

Bleach Catalysts, when used in the present ADD compositions are preferably segregated from the hydrogen peroxide source, or from QSBA's, QSP's, diacyl peroxides, or even from enzymes. A convenient approach, which can have the additional advantage of conferring a protective effect upon enzymes as used herein, is to process the enzymes with a coating of transition metal bleach catalyst, optionally with a waxy nonionic surfactant.

In another mode, transition-metal containing bleach catalysts can be prepared in situ by the reaction of a transition-metal salt with a suitable chelating agent. For example, a mixture of manganese sulfate and EDDS (See Chelating Agent disclosure hereinafter).

When highly colored, transition metal-containing bleach catalysts may be coprocessed with zeolites, such as zeolite A or zeolite P, for example so as to reduce the color impact and improve the aesthetics of the product.

As a practical matter, and not by way of limitation, the ADD compositions and processes herein can be adjusted to provide on the order of at least one part per ten million of the active bleach catalyst species in the aqueous washing medium, and will preferably provide from about 0.1 ppm to about 50 ppm, more preferably from about 1 ppm to about 25 ppm, of the catalyst species in the wash liquor.

Organic Peroxides, especially Diacyl Peroxides—These optional bleach-improving materials are extensively illustrated in Kirk Othmer, Encyclopedia of Chemical Technology, Vol. 17, John Wiley and Sons, 1982 at pages 27–90 and especially at pages 63–72, all incorporated herein by reference. Suitable organic peroxides, especially diacyl peroxides, are further illustrated in "Initiators for Polymer Production", Akzo Chemicals Inc., Product Catalog, Bulletin No. 88-57, incorporated by reference. Preferred diacyl peroxides herein whether in pure or formulated form constitute solids at 25° C., e.g., CADET® BPO 78 powder form of dibenzoyl peroxide, from Akzo. Highly preferred organic peroxides, particularly the diacyl peroxides, herein have melting points above 40° C., preferably above 50° C. Additionally, preferred are the organic peroxides with SADT's (as defined in the foregoing Akzo publication) of 35° C. or higher, more preferably 70° C. or higher. Non-limiting examples of diacyl peroxides useful herein include dibenzoyl peroxide, lauroyl peroxide, and dicumyl peroxide. Dibenzoyl peroxide is preferred. In some instances, diacyl peroxides are available in the trade which contain oily substances such as dioctyl phthalate. In general, it is preferred to use diacyl peroxides which are substantially free from oily phthalates since these can form smears on dishes and glassware.

Stability-Enhanced Amylase—Engineering of enzymes for improved stability, e.g., oxidative stability is known. See, for example J.Biological Chem., Vol. 260, No. 11, June 1985, pp 6518–6521.

"Reference amylase" refers to a conventional amylase inside the scope of the amylase component of this invention. Further, stability-enhanced amylases, also within the invention, are typically compared to these "reference amylases".

The present invention preferably makes use of amylases having improved stability in detergents, especially improved oxidative stability. A convenient absolute stability reference-point against which amylases used in the instant invention represent a measurable improvement is the stability of TERMAMYL® in commercial use in 1993 and available from Novo Nordisk A/S. This TERMAMYL® amylase is a "reference amylase", and is itself well-suited for use in the ADD compositions of the invention. Even more preferred amylases herein share the characteristic of being "stability-enhanced" amylases, characterized, at a minimum, by a measurable improvement in one or more of: oxidative stability, e.g., to hydrogen peroxide/tetraacetylethylenediamine in buffered solution at pH 9–10; thermal stability, e.g., at common wash temperatures such as about 60° C.; or alkaline stability, e.g., at a pH from about 8 to about 11, all measured versus the above-identified reference-amylase. Preferred amylases herein can demonstrate further improvement versus more challenging reference amylases, the latter reference amylases being illustrated by any of the precursor amylases of which preferred amylases within the invention are variants. Such precursor amylases may themselves be natural or be the product of genetic engineering. Stability can be measured using any of the art-disclosed technical tests. See references disclosed in WO 94/02597, itself and documents therein referred to being incorporated by reference.

In general, stability-enhanced amylases respecting the preferred embodiments of the invention can be obtained from Novo Nordisk A/S, or from Genencor International.

Preferred amylases herein have the commonality of being derived using site-directed mutagenesis from one or more of the Baccillus amylases, especialy the Bacillus alpha-amylases, regardless of whether one, two or multiple amylase strains are the immediate precursors.

As noted, "oxidative stability-enhanced" amylases are preferred for use herein despite the fact that the invention makes them "optional but preferred" materials rather than essential. Such amylases are non-limitingly illustrated by the following: (a) An amylase according to the hereinbefore incorporated WO/94/02597, Novo Nordisk A/S, published Feb. 3, 1994, as further illustrated by a mutant in which substitution is made, using alanine or threonine (preferably threonine), of the methionine residue located in position 197 of the *B. licheniformis* alpha-amylase, known as TERMAMYL®, or the homologous position variation of a similar parent amylase, such as *B. amyloliquefaciens, B. subtilis,* or *B. stearothermophilus;* (b) Stability-enhanced amylases as described by Genencor International in a paper entitled "Oxidatively Resistant alpha-Amylases" presented at the 207th American Chemical Society National Meeting, Mar. 13–17 1994, by C. Mitchinson. Therein it was noted that bleaches in automatic dishwashing detergents inactivate alpha-amylases but that improved oxidative stability amylases have been made by Genencor from *B.licheniformis* NCIB8061. Methionine (Met) was identified as the most likely residue to be modified. Met was substituted, one at a time, in positions 8,15,197,256,304,366 and 438 leading to specific mutants, particularly important being M197L and M197T with the M197T variant being the most stable expressed variant. Stability was measured in CASCADE® and SUNLIGHT®; (c) Particularly preferred herein are amylase variants having additional modification in the immediate parent available from Novo Nordisk A/S. These amylases do not yet have a tradename but are those referred to by the supplier as QL37+M197T.

Any other oxidative stability-enhanced amylase can be used, for example as derived by site-directed mutagenesis from known chimeric, hybrid or simple mutant parent forms of available amylases.

Protease Enzymes—Protease enzymes are usually present in preferred embodiments of the invention at levels sufficient to provide from 0.005 to 0.1 Anson units (AU) of activity per gram of composition. The proteolytic enzyme can be of animal, vegetable or microorganism (preferred) origin. More preferred is serine proteolytic enzyme of bacterial origin. Purified or nonpurified forms of enzyme may be used. Proteolytic enzymes produced by chemically or genetically modified mutants are included by definition, as are close structural enzyme variants. Particularly preferred by way of proteolytic enzyme is bacterial serine proteolytic enzyme obtained from Bacillus, *Bacillus subalis* and/or *Bacillus licheniformis*. Suitable commercial proteolytic enzymes include Alcalase®, Esperase®, Durazyme®, Savinase®, Maxatase®, Maxacal®, and Maxapem® 15 (protein engineered Maxacal); Purafect® and subtilisin BPN and BPN' are also commercially available. Preferred proteolytic enzymes also encompass modified bacterial serine proteases, such as those described in European Patent Application Serial Number 87 303761.8, filed Apr. 28, 1987 (particularly pages 17, 24 and 98), and which is called herein "Protease B", and in European Patent Application 199,404, Venegas, published Oct. 29, 1986, which refers to a modified bacterial serine proteolytic enzyme which is called "Protease A" herein. More preferred is what is called herein "Protease C", which is a triple variant of an alkaline serine protease from Bacillus in which tyrosine replaced valine at position 104, serine replaced asparagine at position 123, and alanine replaced threonine at position 274. Protease C is described in EP 90915958:4, corresponding to WO 91/06637, PUblished May 16, 1991, which is incorporated herein by reference. Genetically modified variants, particularly of Protease C, are also included herein. Some preferred proteolytic enzymes are selected from the group consisting of Savinase®, Esperase®, Maxacal®, Purafect®, BPN', Protease A and Protease B, and mixtures thereof. Bacterial serine protease enzymes obtained from *Bacillus subtilis* and/or *Bacillus lichenformis* are preferred. An especially preferred protease herein referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76 in combination with one or more amino acid residue positions equivalent to those selected from the group consisting of +99, +101, +103, +107 and +123 in *Bacillus amyloliquefaciens* subtilisin as described in the concurrently filed patent applications of A. Baeck, C. K. Ghosh, P. P. Greycar, R. R. Bott and L. J. Wilson, entitled "Protease-Containing Cleaning Compositions" having U.S. Ser. No. 08/136,797 (P&G Case 5040), and "Bleaching Compositions Comprising Protease Enzymes" having U.S. Ser. No. 08/136,626, which are incorporated herein by reference.

pH-Adjusting Component—The preferred ADD compositions herein comprise a pH-adjusting component selected from water-soluble alkaline inorganic salts and water-soluble organic or inorganic builders. The pH-adjusting components are selected so that when the ADD is dissolved in water at a concentration of 1,000–5,000 ppm, the pH remains in the range of above about 8, preferably from about 9.5 to about 11. The preferred nonphosphate pH-adjusting component of the invention is selected from the group consisting of:

(i) sodium carbonate or sesquicarbonate;

(ii) sodium silicate, preferably hydrous sodium silicate having $SiO_2:Na_2O$ ratio of from about 1:1 to about 2:1, and mixtures thereof with limited quantites of sodium metasilicate;

(iii) sodium citrate;

(iv) citric acid;

(v) sodium bicarbonate;

(vi) sodium borate, preferably borax;

(vii) sodium hydroxide; and (viii) mixtures of (i)–(vii).

Preferred embodiments contain low levels of silicate (i.e. from about 3% to about 8% $SiO_2$).

Illustrative of highly preferred pH-adjusting component systems are binary mixtures of granular sodium citrate with anhydrous sodium carbonate, and three-component mixtures of granular sodium citrate trihydrate, citric acid monohydrate and anhydrous sodium bicarbonate.

The amount of the pH adjusting component in the instant ADD compositions is preferably from about 1% to about 50%, by weight of the composition. In a preferred embodiment, the pH-adjusting component is present in the ADD composition in an amount from about 5% to about 40%, preferably from about 10% to about 30%, by weight.

For compositions herein having a pH between about 9.5 and about 11 of the initial wash solution, particularly preferred ADD embodiments comprise, by weight of ADD, from about 5% to about 40%, preferably from about 10% to about 30%, most preferably from about 15% to about 20%, of sodium citrate with from about 5% to about 30%, preferably from about 7% to 25%, most preferably from about 8% to about 20% sodium carbonate.

The essential pH-adjusting system can be complemented (i.e. for improved sequestration in hard water) by other optional detergency builder salts selected from nonphosphate detergency builders known in the art, which include the various water-soluble, alkali metal, ammonium or substituted ammonium borates, hydroxysulfonates, polyacetates, and polycarboxylates. Preferred are the alkali metal, especially sodium, salts of such materials. Alternate water-soluble, non-phosphorus organic builders can be used for their sequestering properties. Examples of polyacetate and polycarboxylate builders are the sodium, potassium, lithium, ammonium and substituted ammonium salts of ethylenediamine tetraacetic acid; nitrilotriacetic acid, tartrate monosuccinic acid, tartrate disuccinic acid, oxydisuccinic acid, carboxymethyloxysuccinic acid, mellitic acid, and sodium benzene polycarboxylate salts.

When present, sodium and potassium, especially sodium, silicates are preferred. Particularly preferred alkali metal silicates are granular hydrous sodium silicates having $SiO_2:Na_2O$ ratio of about 2.0 or about 2.4, respectively, available from PQ Corporation, named Britesil H20® and Britesil H24®. Most preferred is a granular hydrous sodium silicate having a $SiO_2:Na_2O$ ratio of 2.0. While typical forms, i.e., powder and granular, of hydrous silicate particles are suitable, preferred silicate particles have a mean particle size between about 300 and about 900 microns with less than 40% smaller than 150 microns and less than 5% larger than 1700 microns. Particularly preferred is a silicate particle with a mean particle size between about 400 and about 700 microns with less than 20% smaller than 150 microns and less than 1% larger than 1700 microns.

Alternate silicate-containing materials which can be used in the pH-adjusting component include zeolites, such as zeolites A and P, including recently described assertedly "maximum aluminium" variants; or, more preferably, layer silicates such as SKS-6: a wide variety of such silicates are available from Hoechst Corp. or from PQ Corp. When used in the instant compositions for pH-adjusting, aluminium anticorrosion or surfactant-absorbing effects, the levels of any limited water-solubility silicates should not be such as to result in deposition on dishware.

Further, silicates such as sodium metasilicate, or sodium hydroxide, may be added to the instant compositions, especially for upward pH adjustment.

Low-Foaming Nonionic Surfactant—ADD compositions of the present invention can comprise low foaming nonionic surfactants (LFNIs). LFNI can be present in amounts from 0 to about 10% by weight, preferably from about 0.25% to about 4%. LFNIs are most typically used in ADDs on account of the improved water-sheeting action (especially from glass) which they confer to the ADD product. They also encompass non-silicone, nonphosphate polymeric materials further illustrated hereinafter which are known to defoam food soils encountered in automatic dishwashing.

Preferred LFNIs include nonionic alkoxylated surfactants, especially ethoxylates derived from primary alcohols, and blends thereof with more sophisticated surfactants, such as the polyoxypropylene/polyoxyethylene/polyoxypropylene reverse block polymers. The PO/EO/PO polymer-type surfactants are well-known to have foam suppressing or alefoaming action, especially in relation to common food soil ingredients such as egg.

The invention encompasses preferred embodiments wherein LFNI is present, and wherein this component is solid at about 95° F. (35° C.), more preferably solid at about 77° F. (25° C.). For ease of manufacture, a preferred LFNI has a melting point between about 77° F. (25° C.) and about 140° F. (60° C.), more preferably between about 80° F.(26.6° C.) and 110° F. (43.3° C.).

In a preferred embodiment, the LFNI is an ethoxylated surfactant derived from the reaction of a monohydroxy alcohol or alkylphenol containing from about 8 to about 20 carbon atoms, excluding cyclic carbon atoms, with from about 6 to about 15 moles of ethylene oxide per mole &alcohol or alkyl phenol on an average basis.

A particularly preferred LFNI is derived from a straight chain fatty alcohol containing from about 16 to about 20 carbon atoms ($C_{16}$–$C_{20}$ alcohol), preferably a $C_{18}$ alcohol, condensed with an average of from about 6 to about 15 moles, preferably from about 7 to about 12 moles, and most preferably from about 7 to about 9 moles of ethylene oxide per mole of alcohol. Preferably the ethoxylated nonionic surfactant so derived has a narrow ethoxylate distribution relative to the average.

The LFNI can optionally contain propylene oxide in an amount up to about 15% by weight. Other preferred LFNI surfactants can be prepared by the processes described in U.S. Pat. No. 4,223,163, issued Sep. 16, 1980, Builloty, incorporated herein by reference.

Highly preferred ADDs herein wherein the LFNI is present make use of ethoxylated monohydroxy alcohol or alkyl phenol and additionally comprise a polyoxyethylene, polyoxypropylene block polymeric compound; the ethoxylated monohydroxy alcohol or alkyl phenol fraction of the LFNI comprising from about 20% to about 80%, preferably from about 30% to about 70%, of the total LFNI.

Suitable block polyoxyethylene-polyoxypropylene polymeric compounds that meet the requirements described hereinbefore include those based on ethylene glycol, propylene glycol, glycerol, trimethylolpropane and ethylenediamine as initiator reactive hydrogen compound. Polymeric compounds made from a sequential ethoxylation and propoxylation of initiator compounds with a single reactive hydrogen atom, such as $C_{12-18}$ aliphatic alcohols, do not generally provide satisfactory suds control in the instant ADDs. Certain of the block polymer surfactant compounds designated PLURONIC® and TETRONIC® by the BASF—Wyandotte Corp., Wyandotte, Mich., are suitable in ADD compositions of the invention.

A particularly preferred LFNI contains from about 40% to about 70% of a polyoxypropylene/polyoxyethylene/polyoxypropylene block polymer blend comprising about 75%, by weight of the blend, of a reverse block co-polymer of polyoxyethylene and polyoxypropylene containing 17 moles of ethylene oxide and 44 moles of propylene oxide; and about 25%, by weight of the blend, of a block co-polymer of polyoxyethylene and polyoxypropylene initiated with trimethylolpropane and containing 99 moles of propylene oxide and 24 moles of ethylene oxide per mole of trimethylolpropane.

Suitable for use as LFNI in the ADD compositions are those LFNI having relatively low cloud points and high hydrophilic-lipophilic balance (HLB). Cloud points of 1% solutions in water are typically below about 32° C. and preferably lower, e.g., 0° C., for optimum control of sudsing throughout a full range of water temperatures.

LFNIs which may also be used include a $C_{18}$ alcohol polyethoxylate, having a degree of ethoxylation of about 8, commercially available as SLF18 from Olin Corp., and any biodegradable LFNI having the melting point properties discussed hereinabove.

Preferred compositions of the present invention can optionally comprise limited quantities (up to about 2%) of nitrogen-containing nonionic surfactants, such as alkyldimethyl amineoxides or fatty glucosamides; when present, such surfactants normally require suds suppression e.g., by silicone suds suppressors.

Anionic Co-surfactant—The automatic dishwashing detergent compositions herein are preferably substantially free from annionic co-surfactants. It has been discovered that certain annionic co-surfactants, particularly fatty carboxylic acids, can cause unsightly films on dishware. Moreover, may anionic surfactants are high foaming. Without intending to be limited by theory, it is believed that such anionic co-surfactants can interact with the quaternary substituted bleach activator and reduce its performance. If present, the anionic co-surfactant is typically of a type having good solubility in the presence of calcium. Such anionic co-surfactants are further illustrated by sulfobetaines, alkyl(polyethoxy)sulfates (AES), alkyl (polyethoxy)carboxylates, and short chained $C_6$–$C_{10}$ alkyl sulfates.

Silicone and Phosphate Ester Suds Suppressors—The ADD's of the invention can optionally contain an alkyl phosphate ester suds suppressor, a silicone suds suppressor, or combinations thereof. Levels in general are from 0% to about 10%, preferably, from about 0.001% to about 5%. Typical levels tend to be low, e.g., from about 0.01% to about 3% when a silicone suds suppressor is used. Preferred non-phosphate compositions omit the phosphate ester component entirely.

Silicone suds suppressor technology and other defoaming agents useful herein are extensively documented in "Defoaming, Theory and Industrial Applications", Ed., P. R. Garrett, Marcel Dekker, N.Y., 1973, ISBN 0-8247-8770-6, incorporated herein by reference. See especially the chapters entitled "Foam control in Detergent Products" (Ferch et al) and "Surfactant Antifoams" (Blease et al). See also U.S. Pat. Nos. 3,933,672 and 4,136,045. Highly preferred silicone suds suppressors are the compounded types known for use in laundry detergents such as heavy-duty granules, although types hitherto used only in heavy-duty liquid detergents may also be incorporated in the instant compositions. For example, polydimethylsiloxanes having trimethylsilyl or alternate endblocking units may be used as the silicone. These may be compounded with silica and/or with surface-active nonsilicon components, as illustrated by a suds suppressor comprising 12% silicone/silica, 18% stearyl alcohol and 70% starch in granular form. A suitable commercial source of the silicone active compounds is Dow Corning Corp.

Levels of the suds suppressor depend to some extent on the sudsing tendency of the composition, for example, an ADD for use at 2000 ppm comprising 2% octadecyldimethylamine oxide may not require the presence of a suds suppressor. Indeed, it is an advantage of the present invention to select cleaning-effective amine oxides which are inherently much lower in foam-forming tendencies than the typical coco amine oxides. In contrast, formulations in which amine oxide is combined with a high-foaming anionic cosurfactant, e.g., alkyl ethoxy sulfate, benefit greatly from the presence of suds suppressor.

Phosphate esters have also been asserted to provide some protection of silver and silver-plated utensil surfaces; however, the instant compositions can have excellent silvercare without a phosphate ester component. Without being limited by theory, it is believed that lower pH formulations, e.g., those having pH of 9.5 and below, plus the presence of the low level amine oxide, both contribute to improved silver care.

If it is desired nonetheless to use a phosphate ester, suitable compounds are disclosed in U.S. Pat. No. 3,314,891, issued Apr. 18, 1967, to Schmolka et al, incorporated herein by reference. Preferred alkyl phosphate esters contain from 16–20 carbon atoms. Highly preferred alkyl phosphate esters are monostearyl acid phosphate or monooleyl acid phosphate, or salts thereof, particularly alkali metal salts, or mixtures thereof.

It has been found preferable to avoid the use of simple calcium-precipitating soaps as antifoams in the present compositions as they tend to deposit on the dishware. Indeed, phosphate esters are not entirely free of such problems and the formulator will generally choose to minimize the content of potentially depositing antifoams in the instant compositions.

Enzymes other than amylase or protease (including enzyme adjuncts)—Optionally, additional enzymes can be included in the formulations herein for a wide variety of substrate cleaning purposes, including removal of colored or triglyceride-based stains. Such enzymes include lipases, cellulases, and peroxidases, as well as mixtures thereof. Other types of enzymes of any suitable origin, such as vegetable, animal, bacterial, fungal and yeast origin, may be added to further supplement the cleaning, stain-removing or anti-spotting action.

When present, lipases comprise from about 0.001 to about 0.01% of the instant compositions and are optionally combined with from about 1% to about 5% of a surfactant having limesoap-dispersing properties, such as an alkyldimethylamine N-oxide or a sulfobetaine. Suitable lipases for use herein include those of bacterial, animal and fungal origin, including those from chemically or genetically modified mutants. Suitable bacterial lipase include those produced by Pseudomonas, such as *Pseudoraonas Stutzeri* ATCC 19.154 as disclosed in GB 1,372,034. Suitable lipases include those which provide a positive immunologieal cross-reaction with the antibody of the lipase produced from the micro-organism *Pseudomonas fluorescens* IAM 1057. This lipase and a method for its production have been described in JP 53-20487, Laid-Open Feb. 24, 1978. This lipase is available under the tradename Lipase P Amano, hereinafter "Amano-P". For additional lipase disclosures, see also U.S. Pat. No. 4,707,291, EP-B 0218272, EP-A 339,681, EP-A 385,401, and PCT/DK 88/00177.

When incorporating lipases into the instant compositions, their stability and effectiveness may in certain instances be enhanced by combining them with small amounts (e.g., less than 0.5% of the composition) of oily but non-hydrolyzing materials.

Peroxidase enzymes are optionally useful in the present invention. They are used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813, published Oct. 19, 1989, by O. Kirk, assigned to Novo Industries A/S.

Enzyme Stabilizing System—The enzyme-containing compositions, especially liquid compositions, herein may comprise from about 0.001% to about 10%, preferably from about 0.005% to about 8%, most preferably from about 0.01% to about 6%, by weight of an enzyme stabilizing system. The enzyme stabilizing system can be any stabilizing system which is compatible with the detersive enzyme. Such stabilizing systems can comprise calcium ion, boric acid, propylene glycol, short chain carboxylic acid, boronic acid, and mixtures thereof.

The stabilizing system of the ADDs herein may further comprise from 0 to about 10%, preferably from about 0.01% to about 6% by weight, of chlorine bleach scavengers, added to prevent chlorine bleach species present in many water supplies from attacking and inactivating the enzymes, especially under alkaline conditions. While chlorine levels in water may be small, typically in the range from about 0.5 ppm to about 1.75 ppm, the available chlorine in the total volume of water that comes in contact with the enzyme during dishwashing is usually large; accordingly, enzyme stability in-use can be problematic.

Suitable chlorine scavenger anions are widely known and readily available, and are illustrated by salts containing ammonium cations or sulfite, bisulfite, thiosulfite, thiosulfate, iodide, etc. Antioxidants such as carbamate, ascorbate, etc., organic amines such as ethylenediaminetetracetic acid (EDTA) or alkali metal salt thereof, monoethanolamine (MEA), and mixtures thereof can likewise be used. Other conventional scavengers such as bisulfate, nitrate, chloride, sources of hydrogen peroxide such as sodium perborate tetrahydrate, sodium perborate monohydrate and sodium percarbonate, as well as phosphate, condensed phosphate, acetate, benzoate, citrate, formate, lactate, malate, tanrate, salicylate, etc., and mixtures thereof can be used if desired. In general, since the chlorine scavenger function can be performed by several of the ingredients separately listed under better recognized functions, (e.g., other components of the invention such as sodium perborate), there is no requirement to add a separate chlorine scavenger unless a compound performing that function to the desired extent is absent from an enzyme-containing embodiment of the invention; even then, the scavenger is added only for optimum results. Moreover, the formulator will exercise a chemist's normal skill in avoiding the use of any scavenger which is majody incompatible with other ingredients, if used. In relation to the use of ammonium salts, such salts can be simply admixed with the detergent composition but are prone to adsorb water and/or liberate ammonia during storage. Accordingly, such materials, if present, are desirably protected in a particle such as that described in U.S. Pat. No. 4,652,392, Baginski et al.

Chelating Agents—The ADD compositions herein may also optionally contain one or more iron and/or manganese chelating agents, such as hydroxyethyldiphosphonate (HEDP). More generally, chelating agents suitable for use herein can be selected from the group consisting of amino carboxylates, amino phosphonates, polyfunctionally-substituted aromatic chelating agents and mixtures thereof. Without intending to be bound by theory, it is believed that the benefit of these materials is due in pan to their exceptional ability to remove iron and manganese ions from washing solutions by formation of soluble chelates; other dishwashing benefits include inorganic film or scale prevention. Other suitable chelating agents for use herein are the commercial DEQUEST series, and chelants from Nalco, Inc.

Aminocarboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts thereof and mixtures thereof.

Aminophosphonates are also suitable for use as chelating agents in the compositions of the invention when at least low levels of total phosphorus are permitted in detergent compositions, and include ethylenediaminetetrakis (methylenephosphonates) Preferably, these aminophosphonates do not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type are dihydroxydisulfobenzenes such as 1,2-dihydroxy-3,5-disulfobenzene.

A highly preferred biodegradable chelator for use herein is ethylenediamine disuccinate ("EDDS"), especially (but not limited to) the [S,S] isomer as described in U.S. Pat. No. 4,704,233, Nov. 3, 1987, to Hartman and Perkins. The trisodium salt is preferred, although other salts such as the Magnesium salts can be used.

If utilized, these chelating agents or transition-metal selective sequestrants will generally comprise from about 0.001% to about 10%, more preferably from about 0.05% to about 1% by weight of the ADD compositions herein.

Dispersant Polymer—Preferred ADD compositions herein may additionally contain a dispersant polymer. When present, a dispersant polymer in the instant ADD compositions is typically at levels in the range from 0 to about 25%, preferably from about 0.5% to about 20%, more preferably from about 1% to about 8% by weight of the ADD composition. Dispersant polymers are useful for improved filming performance of the present ADD compositions, especially in higher pH embodiments, such as those in which wash pH exceeds about 9.5. Particularly preferred are polymers which inhibit the deposition of calcium carbonate or magnesium silicate on dishware.

Dispersant polymers suitable for use herein are further illustrated by the film-forming polymers described in U.S. Pat. No. 4,379,080 (Murphy), issued Apr. 5, 1983.

Suitable polymers are preferably at least partially neutralized or alkali metal, ammonium or substituted ammonium (e.g., mono-, di- or triethanolammonium) salts of polycarboxylic acids. The alkali metal, especially sodium salts are most preferred. While the molecular weight of the polymer can vary over a wide range, it preferably is from about 1,000 to about 500,000, more preferably is from about 1,000 to about 250,000, and most preferably, especially if the ADD is for use in North American automatic dishwashing appliances, is from about 1,000 to about 5,000.

Other suitable dispersant polymers include those disclosed in U.S. Pat. No. 3,308,067 issued Mar. 7, 1967, to Diehl. Unsaturated monomeric acids that can be polymerized to form suitable dispersant polymers include acrylic acid, maleic acid (or maleic anhydride), fumaric acid, itaconic acid, aconitic acid, mesaconic acid, citraconic acid and methylenemalonic acid. The presence of monomedc segments containing no carboxylate radicals such as methyl vinyl ether, styrene, ethylene, etc. is suitable provided that such segments do not constitute more than about 50% by weight of the dispersant polymer.

Copolymers of acrylamide and acrylate having a molecular weight of from about 3,000 to about 100,000, preferably from about 4,600 to about 20,000, and an acrylamide content of less than about 50%, preferably less than about 20%, by weight of the dispersant polymer can also be used. Most preferably, such dispersant polymer has a molecular weight of from about 4,000 to about 20,000 and an acrylamide content of from about 0% to about 15%, by weight of the polymer.

Particularly preferred dispersant polymers are low molecular weight modified polyacrylate copolymers. Such copolymers contain as monomer units: a) from about 90% to about 10%, preferably from about 80% to about 20% by weight acrylic acid or its salts and b) from about 10% to about 90%, preferably from about 20% to about 80% by weight of a substituted acrylic monomer or its salt and have the general formula: $-[C(R^2)C(R^1)(C(O)OR^3)]$ wherein the apparently unfilled valencies are in fact occupied by hydrogen and at least one of the substituents $R^1$, $R^2$, or $R^3$, preferably $R^1$ or $R^2$, is a 1 to 4 carbon alkyl or hydroxyalkyl group; $R^1$ or $R^2$ can be a hydrogen and $R^3$ can be a hydrogen or alkali metal salt. Most preferred is a substituted acrylic monomer wherein $R^1$ is methyl, $R^2$ is hydrogen, and $R^3$ is sodium.

Suitable low molecular weight polyacrylate dispersant polymer preferably has a molecular weight of less than about 15,000, preferably from about 500 to about 10,000, most preferably from about 1,000 to about 5,000. The most preferred polyacrylate copolymer for use herein has a molecular weight of about 3,500 and is the fully neutralized form of the polymer comprising about 70% by weight acrylic acid and about 30% by weight methacrylic acid.

Other suitable modified polyacrylate copolymers include the low molecular weight copolymers of unsaturated aliphatic carboxylic acids disclosed in U.S. Pat. Nos. 4,530,766, and 5,084,535.

Agglomerated forms of the present ADD compositions may employ aqueous solutions of polymer dispersants as liquid binders for making the agglomerate (particularly when the composition consists of a mixture of sodium citrate and sodium carbonate). Especially preferred are polyacrylates with an average molecular weight of from about 1,000 to about 10,000, and acrylate/maleate or acrylate/fumarate copolymers with an average molecular weight of from about 2,000 to about 80,000 and a ratio of acrylate to maleate or fumarate segments of from about 30:1 to about 1:2. Examples of such copolymers based on a mixture of unsaturated mono- and dicarboxylate monomers are disclosed in European Patent Application No. 66,915, published Dec. 15, 1982.

Other dispersant polymers useful herein include the polyethylene glycols and polypropylene glycols having a molecular weight of from about 950 to about 30,000 which can be obtained from the Dow Chemical Company of Midland, Mich. Such compounds for example, having a melting point within the range of from about 30° C. to about 100° C., can be obtained at molecular weights of 1,450, 3,400, 4,500, 6,000, 7,400, 9,500, and 20,000. Such compounds are formed by the polymerization of ethylene glycol or propylene glycol with the requisite number of moles of ethylene or propylene oxide to provide the desired molecular weight and melting point of the respective polyethylene glycol and polypropylene glycol. The polyethylene, polypropylene and mixed glycols are referred to using the formula: $HO(CH_2CH_2O)_m(CH_2CH(CH_3)O)_n(CH(CH_3)CH_2O)_oOH$ wherein m, n, and o are integers satisfying the molecular weight and temperature requirements given above.

Yet other dispersant polymers useful herein include the cellulose sulfate esters such as cellulose acetate sulfate, cellulose sulfate, hydroxyethyl cellulose sulfate, methylcellulose sulfate, and hydroxypropylcellulose sulfate. Sodium cellulose sulfate is the most preferred polymer of this group.

Other suitable dispersant polymers are the carboxylated polysaccharides, particularly starches, celluloses and alginates, described in U.S. Pat. No. 3,723,322, Diehl, issued Mar. 27, 1973; the dextrin esters of polycarboxylic acids disclosed in U.S. Pat. No. 3,929,107, Thompson, issued Nov. 11, 1975; the hydroxyalkyl starch ethers, starch esters, oxidized starches, dextrins and starch hydrolysates described in U.S. Pat No. 3,803,285, Jensen, issued Apr. 9, 1974; the carboxylated starches described in U.S. Pat. No. 3,629,121, Eldib, issued Dec. 21, 1971; and the dextrin starches described in U.S. Pat. No. 4,141,841, McDonald, issued Feb. 27, 1979. Preferred cellulose-derived dispersant polymers are the carboxymethyl celluloses.

Yet another group of acceptable dispersants are the organic dispersant polymers, such as polyaspartate.

Corrosion Inhibitors/Anti-Tarnish Aids—The present ADD compositions may contain one or more corrosion inhibitors or anti-tarnish aids. Such materials are preferred components of machine dishwashing compositions especially in certain European countries where the use of electroplated nickel silver and sterling silver is still comparatively common in domestic flatware, or when aluminium protection is a concern and the composition is low in silicate. When present, such protecting materials are preferably incorporated at low levels, e.g., from about 0.01% to about 5% of the ADD composition. Suitable corrosion inhibitors include paraffin oil, typically a predominantly branched aliphatic hydrocarbon having a number of carbon atoms in the range of from about 20 to about 50; preferred paraffin oil is selected from predominantly branched $C_{25-45}$ species with a ratio of cyclic to noncyclic hydrocarbons of about 32:68. A paraffin oil meeting those characteristics is sold by Wintershall, Salzbergen, Germany, under the trade name WINOG 70.

Other corrosion inhibitor compounds include benzotriazole and comparable compounds; mercaptans or thiols including thionaphtol and thioanthranol; and finely divided Aluminium fatty acid salts, such as aluminium tristearate. The formulator will recognize that such materials will generally be used judiciously and in limited quantities so as to avoid any tendency to produce spots or films on glassware or to compromise the bleaching action of the compositions. For this reason, mercaptan anti-tarnishes which are quite strongly bleach-reactive and common fatty carboxylic acids which precipitate with calcium in particular are preferably avoided.

Other Optional Adjuncts—Depending on whether a greater or lesser degree of compactness is required, filler materials can also be present in the instant ADDs. These include sucrose, sucrose esters, sodium sulfate, potassium sulfate, etc., in mounts up to about 70%, preferably from 0% to about 40% of the ADD composition. Preferred filler is sodium sulfate, especially in good grades having at most low levels of trace impurities.

Sodium sulfate used herein preferably has a purity sufficient to ensure it is non-reactive with bleach; it may also be treated with low levels of sequestrants, such as phosphonates or EDDS in magnesium-salt form. Note that preferences, in terms of purity sufficient to avoid decomposing bleach, applies also to pH-adjusting component ingredients, specifically including any silicates used herein.

Although optionally present in the instant compositions, the present invention encompasses embodiments which are substantially free from sodium chloride or potassium chloride and total chloride content may be further limited when using QSBA's or QSP's by use of alternative counter-anions to chloride, such as are illustrated by p-toluenesulfonate.

Hydrotrope materials such as sodium benzene sulfonate, sodium toluene sulfonate, sodium cumene sulfonate, etc., can be present, e.g., for better dispersing surfactant.

Bleach-stable perfumes (stable as to odor); and bleach-stable dyes such as those disclosed in U.S. Pat. No. 4,714,562, Roselle et al, issued Dec. 22, 1987 can also be added to the present compositions in appropriate amounts. Other common detergent ingredients consistent with the spirit and scope of the present invention are not excluded.

Since ADD compositions herein can contain water-sensitive ingredients or ingredients which can co-react when brought together in an aqueous environment, it is desirable to keep the free moisture content of the ADDs at a minimum, e.g., 7% or less, preferably 4% or less of the ADD; and to provide packaging which is substantially impermeable to water and carbon dioxide. Coating measures have been described herein to illustrate a way to protect the ingredients from each other and from air and moisture. Plastic bottles, including refillable or recyclable types, as well as conventional barrier cartons or boxes are another helpful means of assuring maximum shelf-storage stability. As noted, when ingredients are not highly compatible, it may further be desirable to coat at least one such ingredient with a low-foaming nonionic surfactant for protection. There are numerous waxy materials which can readily be used to form suitable coated particles of any such otherwise incompatible components; however, the formulator prefers those materials which do not have a marked tendency to deposit or form films on dishes including those of plastic construction.

Method for Cleaning—The present invention also encompasses a method for cleaning soiled tableware comprising contacting said tableware with an aqueous medium having an initial pH in a wash solution of above about 8, more preferably from about 9.5 to about 12, most preferably from about 9.5 to about 10.5 and comprising at least about 500 ppm of an ADD composition comprising the QSBA's as hereinbefore defined.

This invention also encompasses a method of washing tableware in a domestic automatic dishwashing appliance, comprising treating the soiled tableware in an automatic dishwasher with an aqueous alkaline bath comprising amylase and an aliphatic cationic peracid. A preferred method of washing tableware in a domestic automatic dishwashing appliance, comprises treating the soiled tableware wherein said method comprises a step of forming an aliphatic cationic peracid in-situ by reacting a quaternary substituted bleach activator having a caprolactam or valerolactam leaving-group and a source of hydrogen peroxide.

Some preferred substantially chlorine bleach-free granular automatic dishwashing compositions of the invention are as follows:

A substantially chlorine-bleach free automatic dishwashing composition comprising amylase (e.g., TERMAMYL®) and a bleach system consisting essentially of a source of hydrogen peroxide selected from sodium perborate and sodium percarbonate; a QSBA as defined herein, a manganese or iron-containing transition metal bleach catalyst, and a diacyl peroxide;

A substantially chlorine-bleach free automatic dishwashing composition comprising an oxidative stability-enhanced amylase and a bleach system consisting essentially of a source of hydrogen peroxide selected from sodium perborate and sodium percarbonate; and a bleach-improving material which is a mixture of a QSBA and a diacyl peroxide; and A substantially chlorine-bleach free automatic dishwashing composition comprising amylase (e.g., TERMAMYL®) and a bleach system consisting essentially of a source of hydrogen peroxide selected from sodium perborate and sodium percarbonate; and a bleach-improving material which is a mixture of a QSBA and a manganese or iron-containing transition metal bleach catalyst such as a manganese EDDS salt.

Simple but highly effective preferred embodiments are illustrated by a substantially chlorine-bleach free automatic dishwashing composition comprising a conventional amylase, such as TERMAMYL®, and a bleach system consisting essentially of a source of hydrogen peroxide selected from sodium perborate and sodium percarbonate; and a bleach-improving material which is a QSBA substantially free from other bleach-improving materials. Also suitably, there is contemplated a substantially chlorine-bleach free automatic dishwashing composition comprising an oxidative stability-enhanced amylase and a bleach system consisting essentially of a source of hydrogen peroxide selected from sodium perborate and sodium percarbonate; and a QSBA plus TAED or NOBS.

In the above embodiments, where present, highly preferred illustrative examples of the aforementioned bleach-improving materials are as follows:

i) the organic peroxide is preferably dibenzoyl peroxide;
ii) the quaternary substituted bleach activator preferably consists essentially of one or more compounds according to Examples 1–5 hereinafter.
iii) the quaternary substituted peracid is the peracid corresponding to the peracid generated when compounds (ii) perhydrolyze or is absent from the automatic dishwashing composition as formulated (although it may be generated in situ during the wash when compounds (ii) perhydrolyze; and
iv) the transition metal bleach catalyst is a transition metal complex, such as an iron or manganese complex of ethylenediaminedisuccinate; or (less preferably) is $Mn^{IV}_2(u\text{-}O)_3(1,4,7\text{-trimethyl-}1,4,7\text{-triazacyclononane})_2(PF_6)_2$.

Highly preferred compositions substantially free from chlorine bleach and phosphate builder comprise:

a) from about 3.3% to about 33%, by weight of composition, of said hydrogen peroxide source selected from the group consisting of percarbonate, perborate, and mixtures thereof;

b) from about 0.1% to about 10%, by weight of composition, of said quaternary substituted bleach activator;

c) from 0% to about 3% of a diacyl peroxide; and d) from 0% to about 2% of a transition-metal bleach catalyst. Optionally conventional non-charged bleach activators may be included in the compositions. The preferred automatic dishwashing composition further comprise from about 0.1% to about 10% of a low foaming nonionic surfactant and are substantially free of anionic surfactant. Other preferred embodiments include said automatic dishwashing composition further comprising from about 1% to about 50%, by weight of composition, of a pH adjusting component. The pH adjusting component preferably provides a wash solution pH of at least 8.

A preferred granular or powdered automatic dishwashing detergent composition comprises, by weight:

(a) from about 0.1% to about 10% of quaternary substituted bleach activators of this invention, preferably have a melting-point of at least 30° C.;

(b) from about 1% to about 5%, on an available oxygen basis, of hydrogen peroxide source selected from the group consisting of percarbonate, perborate and mixtures thereof;

(c) from about 0.1% to about 5% of an amylase;

(d) from about 0.1% to about 5% of a protease;

(e) from about 1% to about 50% of a pH adjusting component, said component providing an initial wash solution pH from about 9.5 to about 11;

(f) from about 0.1% to about 10% of a low-foaming nonionic surfactant;

(g) from about 0.1% to about 25% of a dispersant polymer;

(h) from 0% to about 1% of a chelant;

(i) from 0% to about 2% of a silicone suds suppressor;

(j) from 0% to about 3% of dibenzoyl peroxide;

(k) from 0% to about 2% of a transition-metal bleach catalyst; and (l) from 0% to about 5% of a conventional bleach activator.

The following nonlimiting examples further illustrate QSBA compositions and QSBA-containing ADD compositions of the present invention.

EXAMPLE 1

Preparation of the QSBA 6-(N,N,N-Trimethylammonio) hexanoyl Caprolactam p-Toluenesulfonate (compound 5)

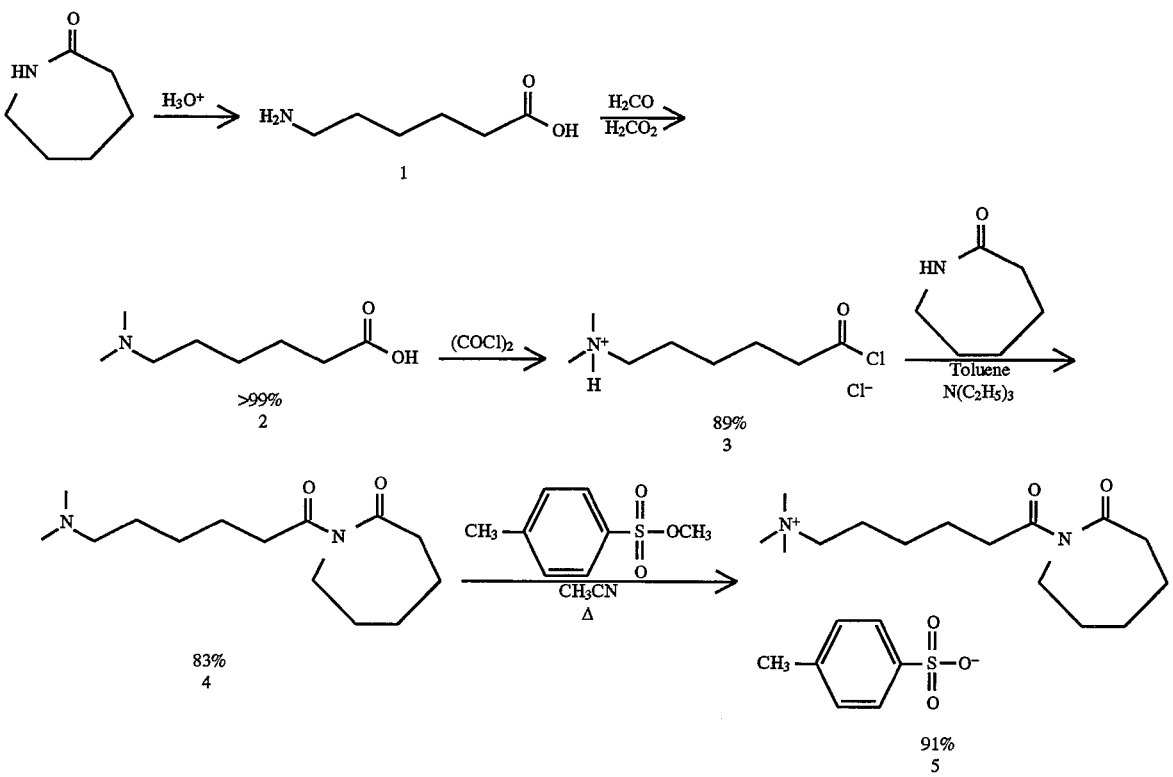

6-(N,N-Dimethylamino)hexanoic acid (2) To a 2000 mL three-necked round-bottomed flask equipped with an internal thermometer and reflux condenser are added 6-aminocaproic acid (200.00 g, 1.53 mol), formaldehyde (357.61 g, 4.41 mol, 37 wt %), and formic acid (454.56 g, 8.69 mol, 88%). Once addition is complete, the mixture is heated to reflux for 3 h, then cooled to room temperature. Analysis by TLC (74:25:1, propanol:water:formic acid, $R_f$=0.45) indicates the reaction is complete. To the crude mixture is added 158 mL of concentrated HCl (36–37%). The mixture is concentrated to dryness by rotary evaporation for 5 h to remove excess formaldehyde and formic acid. The hydrochloride is redissolved in 300 mL of water and neutralized with 132.5 g of 50 wt % NaOH solution to a pH of about 7.0. The mixture is concentrated by rotary evaporation with isopropanol to facilitate drying. The product is leached out from the solids by triturating with dichloromethane. After drying the organic layer over $MgSO_4$ and filtering, the product is isolated by concentrating the organic layer by rotary evaporation and drying under vacuum to give 2 as a white solid, 251.86 g (>99% yield): mp 89°–91° C.

6-(N,N-Dimethylamino)hexanoyl chloride hydrochloride (3) Into a 500 mL three-necked round-bottomed flask equipped with a reflux condenser, internal thermometer, mechanical stirrer, and argon inlet, is placed oxalyl chloride (398.67 g, 3.14 mol). Acid 2 (100 g, 0.63 mol) is added over 30 min while maintaining the reaction temperature at 40° C. As reaction takes place, $CO_2$ and CO are swept away from the mixture with argon. After addition is complete, the mixture is stirred for 2 h while the reaction flask cools to room temperature. Excess oxalyl chloride is removed by rotary evaporation at 50° C. and then by Kugelrohr distillation at 50° C. (0.1 mm Hg) for 2 h. Isolated is 3, 118.98 g (88.5%) as an oil that solidifies on standing.

6-(N,N-Dimethylamino)hexanoyl caprolactam (4) To a 1000 mL three-necked round-bottomed flask equipped with a reflux condenser, internal thermometer, argon inlet, and mechanical stirrer, are added ε-caprolactam (48.04 g, 0.42 mol), toluene (340 mL), and triethylamine (189.00 g, 1.87 mol). The mixture is heated to reflux (ca. 101° C.) for 15 min. While at that temperature, acid chloride 3 (100.00 g, 0.47 mol) is added as a solid over 30 min. The reaction is maintained at reflux for an additional 1.75 h before the heat is removed. At room temperature, the mixture is filtered and the salts washed with toluene. The dark filtrate is washed with saturated sodium bicarbonate solution (3×250 mL), water (100 mL), and dried over $MgSO_4$. The mixture is filtered and concentrated by rotary evaporation at about 50° C. (water aspirator) and then by Kugelrohr distillation at 60° C. for 1 h to give 89.64 g (83%) of 4 as a dark red oil.

6-(N,N,N-Trimethylammonio)hexanoyl caprolactam p-toluenesulfonate (5) In a 500 mL three-necked round-bottomed flask fitted with an argon inlet, condenser, and stir bar are placed amine amide 4 (17.94 g, 0.071 mol), acetonitrile (200 mL), and methyl p-toluenesulfonate (13.13 g, 0.071 mol). While adding the tosylate, the reaction mixture mildly exotherms. The mixture is heated to reflux for 3 h and is then cooled to room temperature. While concentrating the mixture by rotary evaporation, a tan solid forms which is re-dissolved in a minimal amount of acetonitrile and triturated with ether until a free flowing dispersion of the solid is obtained in the solvent system. The solid is collected by vacuum filtration under a blanket of nitrogen and transferred to a round-bottomed flask. The solid product is dried at room temperature under vacuum (0.1 mmHg) for 24 h to give 5 (27.84 g, 90%) as an off-white solid, mp 128°–131° C. (softens at 118° C.).

EXAMPLE 2

(A)—The synthesis of Example 1 is repeated but with substitution of valerolactam for caprolactam as the starting material in the first step.

(B)—The synthesis of Example 1 is repeated but with substitution of valerolactam for caprolactam as the compound reacted with compound 3.

(C)—The synthesis of Example 1 is repeated but with substitution of valerolactam for caprolactam as the starting material in the first step and as the compound reacted with compound 3.

EXAMPLE 3

The synthesis of Example 1 is repeated with the substitution of acetaldehyde for formaldehyde in the preparation of compound 2 in Example 1, and with substitution of Ethyl p-toluenesulfonate for Methyl p-toluenesulfonate in the preparation of compound 5 in Example 1.

EXAMPLE 4

The synthesis of Example 1 is repeated with the substitution of a benzyl for a methyl group on the quaternary nitrogen and with chloride replacing p-toluenesulfonate as the counter-ion. The product has the structure:

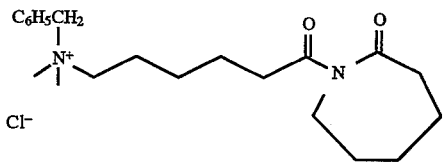

(wherein the unfilled valencies are methyl). In more detail, the synthesis is accomplished as follows: unless otherwise indicated, substitutions are with respect to the reaction outline in Example 1. The synthesis begins with the preparation of N-benzylcaprolactam. (Analogous to caprolactam, the commercial starting compound in Example 1, except that a benzyl group replaces H on N.)

N-Benzylcaprolactam—Sodium hydride (39.77 g, 1.33 mol, 80%) is placed in a three-necked round-bottomed flask and washed with anhydrous toluene (4×30 mL) under argon. Toluene (800 mL) is added and the flask is equipped with a reflux condenser, mechanical stirrer, and addition funnel. A solution of ε-caprolactam (50.00 g, 0.442 mol) in 100 mL of toluene is added over 30 min. After addition is complete, the mixture is heated at reflux for 15 min. Benzyl chloride (83.90 g, 0.663 mol) is added dropwise over 15 min. The mixture is heated at reflux for an additional 1.3 h, cooled to room temperature, and then further cooled to 0° C. The mixture is then carefully neutralized with 95% ethanol and then diluted with water (250 mL). The organic layer is washed with brine (2×200 mL) and water (2×200 mL), dried over MgSO$_4$, filtered, and concentrated by rotary evaporation. The mixture is further concentrated by Kugelrohr distillation at 60° C. (0.2 mm Hg) for 5 h. The product is recrystallized from ether to give 55.56 g (62%) of N-benzylcaprolactam as a white crystalline product.

6-(N-Benzylamino)hexanoic acid—This compound is similar to compound 1 in Example 1, except that a single Benzyl group replaces one of the H atoms bonded at Nitrogen. N-Benzylcaprolactam (80.59 g, 0.396 mol) and concentrated HCl (155 mL) are heated to reflux in a round-bottomed flask with condenser for 14 days. The mixture is cooled to room temperature and concentrated by rotary evaporation to give an off-white solid. The product is isolated in a manner similar to that used to isolate acid 2 in the reaction sequence of Example 1.

6-(N-Benzyl-N-methylamino)hexanoic acid—6-Aminocaproic acid in the preparation of compound 2 in Example 1 is replaced with 6-(N-benzylamino)hexanoic acid to give 6-(N-benzyl-N-methylamino)hexanoic acid.

6-(N-Benzyl-(N-methylamino))hexanoyl chloridehydrochloride—6-(N,N-Dimethylamino)hexanoic acid in the preparation of compound 3 in Example 1 is replaced with 6-(N-benzyl-N-methylamino)hexanoic acid to give 6-(N-benzyl-(N-methyl-amino))hexanoyl chloride-hydrochloride.

6-(N-Benzyl-(N-methylamino))hexanoyl caprolactam—6-(N,N-Dimethylamino)-hexanoyl chloridehydrochloride in the preparation of compound 4 in Example 1 is replaced with 6-(N-benzyl-(N-dimethylamino))hexanoyl chloride.hydrochloride to give 6-(N-benzyl-(N-methylamino))hexanoyl caprolactam.

The final step in the synthesis is accomplished by replacing the methyl p-toluenesulfonate used in the last step of Example 1 using chloromethane.

An alternate and simpler synthesis of the same final product can be accomplished as follows: Compound 4 of Example 1 is reacted with benzyl chloride to directly obtain the final product.

EXAMPLE 5

A QSBA wherein two benzyl groups replace methyl groups on the quaternary nitrogen and wherein chloride replaces p-toluenesulfonate as the counter-ion as compared with compound 5 of Example 1 has the following structure:

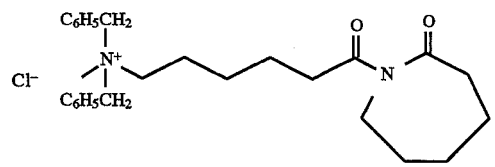

(wherein the unfilled valency is Methyl). The preparation is as follows. Unless otherwise indicated, substitutions are with respect to Example 1.

6-(N,N-Dibenzyl-N-methylammonio)hexanoyl caprolactam chloride—6-(N,N-Di-methylamino)hexanoyl caprolactam in the preparation of compound 5 in Example 1 is replaced with 6-(N-benzyl-(N-methylamino))hexanoyl caprolactam, which is compound 10 as prepared in Example 4; and methyl p-toluenesulfonate as used in Example 1 is replaced with benzyl chloride. This gives the QSBA 6-(N,N-dibenzyl-N-methyl-amino)hexanoyl caprolactam chloride.

EXAMPLE 6

Using preparation techniques similar to those used in the preceding examples, with adaptation within the normal skills of the organic synthetic chemist, the following additional QSBA compounds having formula R$^1$R$^2$R$^3$N$^+$(CH$_2$)$_n$C(O)L X$^-$ are prepared.

| Example 6 | R$^1$ | R$^2$ | R$^3$ | n | L | X— |
| --- | --- | --- | --- | --- | --- | --- |
| A | CH$_3$ | CH$_3$ | CH$_3$ | 5 | CL | Ms |
| B | CH$_3$(CH$_2$)$_{11}$ | CH$_3$ | CH$_3$ | 5 | CL | pTs |
| C | Bz | Bz | CH$_3$ | 5 | CL | pTs |
| D | CH$_3$(CH$_2$)$_8$ | CH$_3$(CH$_2$)$_8$ | CH$_3$ | 5 | CL | Ms |
| E | CH$_3$(CH$_2$)$_8$ | Bz | CH$_3$ | 5 | CL | Ms |
| F | CH$_3$(CH$_2$)$_{11}$(EO)$_3$ | CH$_3$ | CH$_3$ | 5 | CL | Cl— |
| G | Np | CH$_3$ | CH$_3$ | 5 | CL | Cl— |
| H | CH$_3$ | CH$_3$ | CH$_3$ | 6 | CL | pTs |

| Example 6 | R¹ | R² | R³ | n | L | X— |
|---|---|---|---|---|---|---|
| I | CH₃ | CH₃ | CH₃ | 4 | CL | pTs |
| J | CH₃ | CH₃ | CH₃ | 3 | CL | pTs | wherein Np is 1-Naphthylmethylene, Bz is benzyl, EO is $CH_2CH_2O$, CL is caprolactam, Ms is methanesulfonate, pTs is p-toluenesulfonate.

EXAMPLE 7

Using preparation techniques similar to those used in the preceding examples, with adaptation within the normal skills of the organic synthetic chemist, the following additional QSBA compounds having formula $R^1R^2R^3N^+ZC(O)L\ X^-$ are prepared:

| Example 7 | R¹ | R² | R³ | L | X— | Z |
|---|---|---|---|---|---|---|
| A | CH₃ | CH₃ | CH₃ | VL | pTs | p-(C₆H₄)CH₂ |
| B | Bz | Bz | CH₃ | CL | pTs | p-(C₆H₄)CH₂ |
| C | CH₃(CH₂)₇(EO)₃ | CH₃ | CH₃ | CL | pTs | p-(C₆H₄)(CH₂)₃ |

EXAMPLE 8

1,4-Di-(methyl-(6'-(N,N-Dimethylammonio)hexanoyl) caprolactam)benzene dichloride.

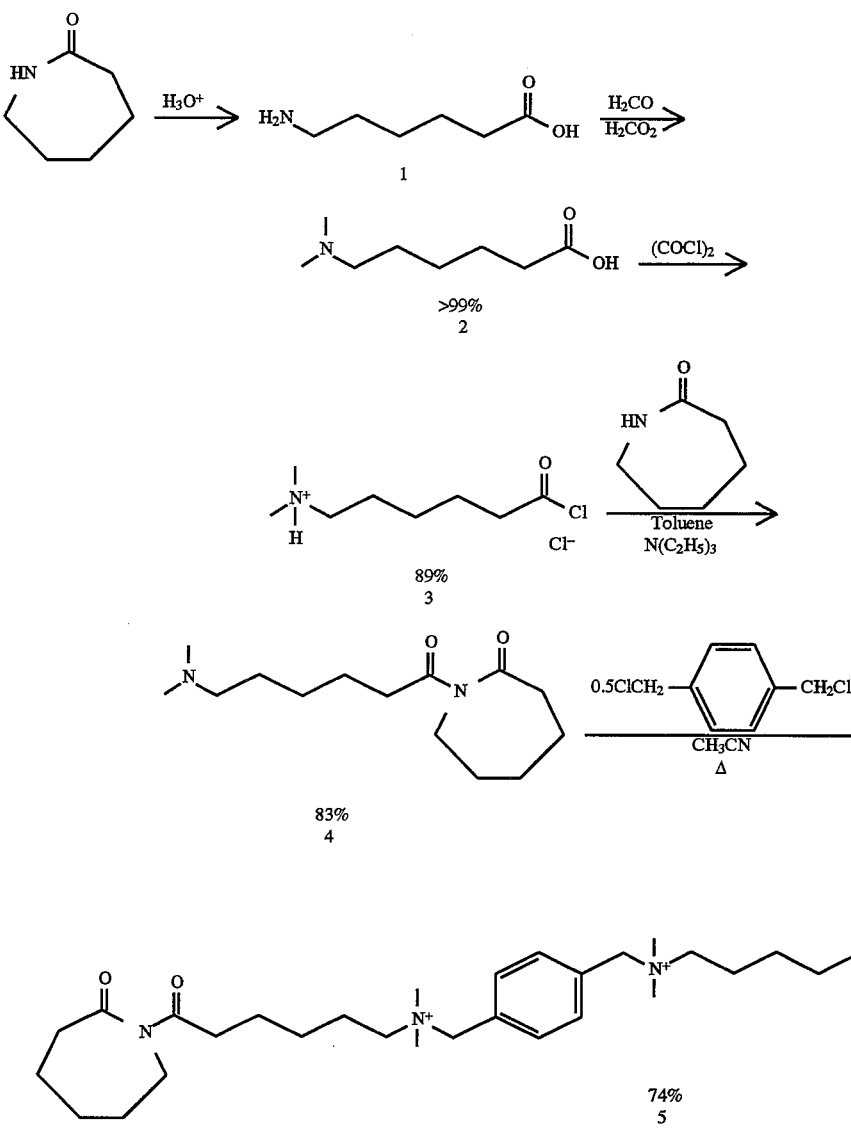

Compounds 1–4 are synthesized as in Example 1. Now, 6-(N,N-Dimethylamino)hexanoyl caprolactam (4) (30.00 g, 0.118 mol) and acetonitrile (150 mL), are placed in a 500 mL three-necked round-bottomed flask fitted with a condenser and argon inlet. To the solution is added α, α'-dichloro-p-xylene (10.32 g, 0.059 mol) dissolved in 50 mL of acetonitrile. The mixture is heated to reflux for 2.5 h, cooled to room temperature, and concentrated by rotary evaporation at 50° C. A brown semi-solid which remains is further concentrated at 60° C. (0.1 mm Hg) for 3 h. The solid is triturated with acetonitrile and ether to remove impurities. The product, having diquaternary structure shown above, is isolated as a solid, 30.00 g (74%).

EXAMPLE 9

N-(4-(caprolactam-N-carbonyl)phenylmethyl)-N-(6'-(N,N-dimethylammonio) hexanoyl) caprolactam) chloride.

6-(N,N-Dimethylamino)hexanoyl caprolactam, 4-chlorobenzoylcaprolactam, and acetonitrile (150 mL) are placed in a 500 mL three-necked round-bottomed flask fitted with a condenser and argon inlet. The mixture is heated to reflux for 2.5 h, cooled to room temperature, and concentrated by rotary evaporation at 50° C. to give N-(4-(caprolactam-N-carbonyl)phenylmethyl)-N-(6'-(N,N-dimethylammonio)-hexanoyl)caprolactam) chloride. The product has the structure:

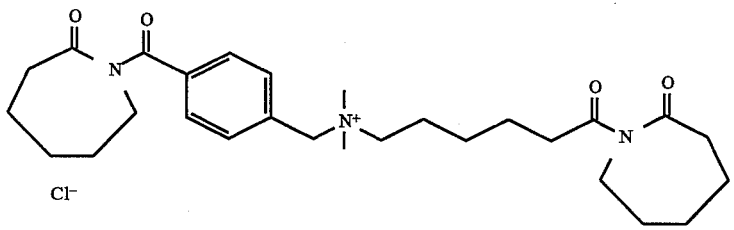

EXAMPLE 10

The following fully-formulated solid-form automatic dishwashing detergents are prepared:

| Example 10 INGREDIENT | 10A wt % | 10B wt % |
|---|---|---|
| QSBA (See Note 2) | 2.6 | 4.4 |
| Sodium Perborate Monohydrate (See Note 4) | 1.5 | 1.5 |
| Amylase (Termamyl® 60T, Novo) | 1 | 0 |
| Transition Metal Bleach Catalyst (See Note 3) | 0.3 | 0 |
| Protease 1 (SAVINASE 12 T, 3.6% active protein) | 2.5 | 0 |
| Protease 2 (Protease D, as 4% active protein) | 0 | 2.5 |
| Trisodium Citrate Dihydrate (anhydrous basis) | 15 | 15 |
| Sodium Carbonate, anhydrous | 20 | 20 |
| BRITESIL H20, PQ Corp. (as SiO$_2$) | 9 | 8 |
| Diethylenetriaminepentaacetic Acid, Sodium Salt | 0 | 0.1 |
| Ethylenediamine Disuccinate, Trisodium Salt | 0.13 | 0 |
| Hydroxyethyldiphosphonate (HEDP), Sodium Salt | 0.5 | 0.5 |
| Dispersant Polymer (See Note 1) | 8 | 8 |
| Nonionic Surfactant (SLF18, Olin Corp. or LF404, BASF) | 2 | 2 |
| Sodium Sulfate, water, minors | Balance to 100% | Balance to 100% |

Note 1: Dispersant Polymer: One or more of: Sokolan PA30, BASF Corp., Accusol 480N, Rohm & Haas.
Note 2: QSBA: Final Product of Example 1. This QSBA may be substituted by use of a QSBA according to any of Examples 2–9.
Note 3: Transition Metal Bleach Catalyst: MnEDDS according to U.S. application Ser. No. 08/210,186, filed March 17, 1994.
Note 4: These hydrogen peroxide sources are expressed on a weight % available oxygen basis. To convert ot a basis of percentage of the total composition, divide by about 0.15.

EXAMPLE 11

The following fully-formulated solid-form automatic dishwashing detergents are prepared:

| Example 11 INGREDIENT | 11A wt % | 11B wt % |
|---|---|---|
| QSBA (See Note 2) | 2.6 | 4.4 |
| Sodium Perborate Monohydrate (See Note 4) | 0 | 0.1 |
| Sodium Percarbonate (See Note 4) | 1.5 | 1.2 |
| Amylase (QL37 + M197T as 3% active protein, NOVO) | 1.5 | 1.5 |
| Transition Metal Bleach Catalyst (See Note 3) | 0.3 | 0 |
| Protease 1 (SAVINASE 12 T, 3.6% active protein) | 2.5 | 0 |
| Protease 2 (Protease D, as 4% active protein) | 0 | 2.5 |
| Trisodium Citrate Dihydrate (anhydrous basis) | 15 | 15 |
| Sodium Carbonate, anhydrous | 20 | 20 |
| BRITESIL H20, PQ Corp. (as SiO$_2$) | 9 | 9 |
| Diethylenetriaminepentaacetic Acid, Sodium Salt | 0 | 0.1 |
| Ethylenediamine Disuccinate, Trisodium Salt | 0.13 | 0 |
| Hydroxyethyldiphosphonate (HEDP), Sodium Salt | 0.5 | 0.5 |
| Dispersant Polymer (See Note 1) | 8 | 8 |
| Nonionic Surfactant (SLF18, Olin Corp. or LF404, BASF) | 2 | 2 |
| Sodium Sulfate, water, minors | Balance to 100% | Balance to 100% |

Note 1: Dispersant Polymer: One or more of: Sokolan PA30, BASF Corp., Accusol 480N, Rohm & Haas.
Note 2: QSBA: Final Product of Example 1. This QSBA may be substituted by use of a QSBA according to any of Examples 2–9.
Note 3: Transition Metal Bleach Catalyst: MnEDDS according to U.S. application Ser. No. 08/210,186, filed March 17, 1994.
Note 4: These hydrogen peroxide sources are expressed on a weight % available oxygen basis. To convert to a basis of percentage of the total composition, divide by about 0.15.

EXAMPLE 12

The following fully-formulated solid-form automatic dishwashing detergents are prepared:

| Example 12 INGREDIENT | 12A wt % | 12B wt % |
|---|---|---|
| QSBA (See Note 2) | 2.6 | 4.4 |
| Sodium Perborate Monohydrate (See Note 4) | 1.5 | 1.5 |
| Amylase (QL37 + M197T as 3% active protein, NOVO) | 1.5 | 1.5 |
| Transition Metal Bleach Catalyst (See Note 3) | 0.3 | 0 |
| Protease 1 (SAVINASE 12 T, 3.6% active protein) | 2.5 | 0 |
| Protease 2 (Protease D, as 4% active protein) | 0 | 2.5 |
| Trisodium Citrate Dihydrate (anhydrous basis) | 15 | 15 |
| Sodium Carbonate, anhydrous | 20 | 20 |
| BRITESIL H20, PQ Corp. (as SiO$_2$) | 9 | 8 |
| Sodium Metasilicate Pentahydrate, (as SiO$_2$) | 0 | 3 |

-continued

| Example 12 INGREDIENT | 12A wt % | 12B wt % |
|---|---|---|
| Diethylenetriaminepentaacetic Acid, Sodium Salt | 0 | 0.1 |
| Ethylenediamine Disuccinate, Trisodium Salt | 0.13 | 0 |
| Hydroxyethyldiphosphonate (HEDP), Sodium Salt | 0.5 | 0.5 |
| Dispersant Polymer (See Note 1) | 8 | 8 |
| Nonionic Surfactant (SLF18, Olin Corp. or LF404, BASF) | 2 | 2 |
| Sodium Sulfate, water, minors | Balance to 100% | Balance to 100% |

Note 1: Dispersant Polymer: One or more of: Sokolan PA30, BASF Corp., Accusol 480N, Rohm & Haas.
Note 2: QSBA: Final Product of Example 1. This QSBA may be substituted by use of a QSBA according to any of Examples 2–9.
Note 3: Transition Metal Bleach Catalyst: MnEDDS according to U.S. application Ser. No. 08/210,186, filed March 17, 1994.
Note 4: These hydrogen peroxide sources are expressed on a weight % available oxygen basis. To convert to a basis of percentage of the total composition, divide by about 0.15.

| Example 13 INGREDIENT | 13A wt % | 13B wt % | 13C wt % |
|---|---|---|---|
| QSBA (See Note 2) | 5 | 3 | 2 |
| Sodium Perboraate Monohydrate (See Note 4) | 1.5 | 0 | 0.5 |
| Sodium Percarbonate (See Note 4) | 0 | 1.0 | 1.2 |
| Amylase (QL37 + M197T as 3% active protein, NOVO) | 2 | 1.5 | 1 |
| Dibenzoyl Peroxide | 0.8 | 0.8 | 3.0 |
| Transition Metal Bleach Catalyst (See Note 3) | 0.01 | 0.05 | 0.05 |
| Nonquaternary Bleach Activator (TAED or NOBS) | 0 | 0 | 0.5 |
| Protease 1 (SAVINASE 12 T, 3.6% active protein) | 2.5 | 0 | 0 |
| Protease 2 (Protease D, as 4% active protein) | 0 | 1 | 1 |
| Trisodium Citrate Dihydrate (anhydrous basis) | 15 | 15 | 15 |
| Sodium Carbonate, anhydrous | 20 | 20 | 20 |
| BRITESIL H2O, PQ Corp. (as SiO$_2$) | 7 | 7 | 17 |
| Sodium Metasilicate Pentahydrate, (as SiO$_2$) | 3 | 0 | 0 |
| Diethylenetriaminepentaacetic Acid, Sodium Salt | 0 | 0.1 | 0 |
| Diethylenetriaminepenta(methylene-phosphonic acid), Sodium Salt | 0.1 | 0 | 0.1 |
| Hydroxyethyldiphosponate (HEDP), Sodium Salt | 0.5 | 0 | 0.5 |
| Dispersant Polymer (See Note 1) | 6 | 5 | 6 |
| Nonionic Surfactant (SLF18, Olin Corp., or LF404, BASF) | 2 | 2 | 3 |
| Sodium Sulfate, water, minors | Balance to 100% | Balance to 100% | Balance to 100% |

Note 1: Dispersant Polymer: One or more of: Sokolan PA30, BASF Corp., Accusol 480N, Rohm & Haas.
Note 2: QSBA: Final Product of Example 1. This QSBA may be substituted by use of a QSBA according to any of Examples 2–9.
Note 3: Transition Metal Bleach Catalyst: MnEDDS according to U.S. application Ser. No. 08/210,186, filed March 17, 1994.
Note 4: These hydrogen peroxide sources are expressed on a weight % available oxygen basis. To convert to a basis of percentage of the total composition, divide by about 0.15.

| Example 14 INGREDIENT | 14A wt % | 14B wt % | 14C wt % |
|---|---|---|---|
| QSBA (See Note 2) | 8 | 3 | 1 |
| Sodium Perborate Monohydrate (See Note 4) | 1 | 2 | 1 |
| Sodium Percarbonate (See Note 4) | 0 | 0 | 0 |
| Amylase (Termamyl ® from NOVO) | 2 | 1.5 | 0 |
| Dibenzoyl Peroxide | 0 | 0.1 | 0 |
| Transition Metal Bleach Catalyst (See Note 3) | 0 | 0.01 | 0.01 |
| Nonquaternary Bleach Activator (TAED or NOBS) | 0 | 0 | 2 |
| Protease 1 (SAVINASE 12 T, 3.6% active protein) | 2.5 | 0 | 0 |
| Protease 2 (Protease D, as 4% active protein) | 0 | 1 | 1 |
| Trisodium Citrate Dihydrate (anhydrous basis) | 15 | 30 | 15 |
| Sodium Carbonate, anhydrous | 20 | 0 | 20 |
| BRITESIL H2O, PQ Corp. (as SiO$_2$) | 7 | 10 | 8 |
| Sodium Metasilicate Pentahydrate, (as SiO$_2$) | 3 | 0 | 1 |
| Diethylenetriaminepentaacetic Acid, Sodium Salt | 0 | 0.1 | 0 |
| Diethylenetriaminepenta(methylene-phosphonic acid), Sodium Salt | 0.1 | 0 | 0.1 |
| Hydroxyethyldiphosponate (HEDP), Sodium Salt | 0.1 | 0 | 0.1 |
| Dispersant Polymer (See Note 1) | 8 | 5 | 6 |
| Nonionic Surfactant (SLF18, Olin Corp., or LF404, BASF) | 1.5 | 2 | 3 |
| Sodium Sulfate, water, minors | Balance to 100% | Balance to 100% | Balance to 100% |

Note 1: Dispersant Polymer: One or more of: Sokolan PA30k, BASF Corp., Accusol 480N, Rohm & Haas.
Note 2: QSBA is the final product of any of Examples 1–9.
Note 3: Transition Metal Bleach Catalyst: MnEDDS according to U.S. application Ser. No. 08/210,186, filed March 17, 1994 or Mn$^{IV}_2$(u-O)$_3$(1,4,7-trimethyl-1,4,7-triazacyclnonane)$_2$(PF$_6$)$_2$.
Note 4: These Hydrogen Peroxide Sources are expressed on an available oxygen basis. To convert to a basis of percentage of the total composition, divide by 0.15

The ADD's of the above dishwashing detergent composition examples are used to wash tea-stained cups, starch-soiled and spaghetti-soiled dishes, milk-soiled glasses, starch, cheese, egg or babyfood-soiled flatware, and tomato-stained plastic spatulas by loading the soiled dishes in a domestic automatic dishwashing appliance and washing using either cold fill, 60° C. peak, or uniformly 45°–50° C. wash cycles with a product concentration of the exemplary compositions of from about 1,000 to about 5,000 ppm, with excellent results.

What is claimed is:

1. A quaternary substituted bleach activator compound of the formula:

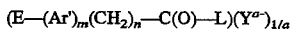

wherein L is selected from caprolactam and valerolactam; E is selected from the group consisting of $R_3N^+$, $R_2(C_6H_5CH_2)N^+$, $R_2(C_6H_5CH_2)_2N^+$, $R_2(N_p)N^+$, and mixtures thereof; R is independently selected from the group consisting of methyl, ethyl, propyl, butyl, phenyl, benzyl, and mixtures thereof; $N_p$ is 1-naphthylmethylene or 2-naphthylmethylene; Ar' is ($C_6H_4$); m is 0 or 1; n is from 0 to about 12, provided that when m is 0, n is not less than 2; Y is a charge balancing compatible anion selected from the group consisting of chloride, bromide, phosphate, sulfate, isethionate, methansulfonate, ethansulfonate, benzenesulfonate, p-toluenesulfonate, cumenesulfonate, xylenesulfonate, naphthalene sulfonate, methyl sulfate, ethyl sulfate, octyl sulfate, terephthalate, polyacrylate having a molecular weight of from about 1,000 to about 4,500, polymaleate having a molecular weight of from about 1,000 to about 4,500, poly(acrylate-comaleate) having a molecular weight of from about 1,000 to about 4,500, benzoate, naphthoate, p-toluate, and mixtures thereof and a is 1 or higher.

2. A compound according to claim 1 wherein R is selected from the group consisting of methyl, ethyl, propyl, benzyl, an mixtures thereof; Y is selected from the group consisting of methyl sulfate, ethyl sulfate, chloride, bromide, p-toluenesulfate, and mixtures thereof, and m is 0.

3. A compound according to claim 2 wherein L is caprolactam.

4. A compound according to claim 3 wherein the quaternary substituted bleach activator is $(CH_3)N^+(CH_2)_5C(O)L$ $(pTs)^-$ wherein L is caprolactam and pTs is p-toluenesulfonate.

* * * * *